United States Patent [19]
Blade et al.

[11] Patent Number: 5,114,940
[45] Date of Patent: May 19, 1992

[54] PESTICIDES

[76] Inventors: Robert J. Blade; Robert J. Peek; George S. Cockerill, all of Wellcome Research Laboratories, Ravens Lane, Berkhamsted, Herts, HP4 2DY, England

[21] Appl. No.: 355,976

[22] Filed: May 22, 1989

Related U.S. Application Data

[63] Continuation-in-part of Ser. No. 269,968, Nov. 10, 1988, abandoned.

[30] Foreign Application Priority Data

Nov. 14, 1987 [GB] United Kingdom ............... 8726735

[51] Int. Cl.$^5$ ................. A61K 31/47; C07D 215/36
[52] U.S. Cl. .................................. 514/248; 514/249; 514/259; 514/300; 514/309; 514/312; 514/367; 544/224; 544/241; 544/283; 544/353; 544/356; 546/146; 546/141; 546/157; 546/122; 548/179; 548/171
[58] Field of Search ............... 514/248, 249, 259, 309, 514/312, 367, 300; 548/248, 171; 546/146, 175, 141, 157, 122; 544/224, 283, 353, 239, 286, 354

[56] References Cited

U.S. PATENT DOCUMENTS

| | | | |
|---|---|---|---|
| 4,736,065 | 4/1988 | Elliot et al. | 564/180 |
| 4,788,204 | 11/1988 | Benavides et al. | 544/283 |

FOREIGN PATENT DOCUMENTS

| | | |
|---|---|---|
| 730347 | 3/1968 | Belgium . |
| 111105 | 10/1982 | European Pat. Off. . |
| 143593 | 11/1983 | European Pat. Off. . |
| 164187 | 2/1985 | European Pat. Off. . |
| 194764 | 2/1985 | European Pat. Off. . |
| 225011 | 9/1985 | European Pat. Off. . |
| 228853 | 12/1985 | European Pat. Off. . |
| 2757483 | 12/1977 | Fed. Rep. of Germany . |
| 2757506 | 12/1977 | Fed. Rep. of Germany . |
| 232699 | 11/1983 | Fed. Rep. of Germany . |
| 3404401 | 2/1984 | Fed. Rep. of Germany . |
| 57-212150 | 6/1981 | Japan . |
| 1514709 | 7/1974 | United Kingdom . |

OTHER PUBLICATIONS

Morrison and Boyd, Organic Chemistry, (Allyn and Bacon, Boston, 1979) pp. 714–716 and 1018–1020.

*Primary Examiner*—Mukund J. Shah
*Assistant Examiner*—E. C. Ward
*Attorney, Agent, or Firm*—Nixon & Vanderhye

[57] ABSTRACT

Compound of the formula (I) are disclosed $$ArQQ^1C(=X)NHR^1 \qquad (I)$$

or a salt thereof, wherein Ar is an optionally substituted polycyclic ring system containing n rings, where n is the integer 2 or 3, at least n-1 rings being aromatic and containing one to three ring nitrogen atoms and optionally containing one or more additional heteroatoms; Q is an alkyl chain containing 1 to 12 carbon atoms and optionally containing a sulphur or one or two oxygen atoms; $Q^1$ is a group $(C(R^2)=C(R^3))_a-(C(R^4)=C(R^5))$ wherein a is 0 or 1, $R^2$, $R^3$, $R^4$ and $R^5$ are the same or different, at least two being hydrogen and the other two being independently selected from hydrogen, halo, $C_{1-4}$ haloalkyl; X is oxygen or sulphur; and $R^1$ is selected from hydrogen and $C_{1-8}$ hydrocarbyl optionally substituted by dioxalanyl, halo, cyano, trifluoromethyl, trifluoromethylthio or $C_{1-6}$ alkoxy are described which have activity particularly against arthropod pests. Pesticidal formulations containing the compounds of the formula (1), their use in the control of pests and method for their preparation are also disclosed.

16 Claims, No Drawings

PESTICIDES

CROSS-REFERENCE TO RELATED APPLICATIONS

This application is a continuation-in-part of earlier application Ser. No. 07/269,968 filed Nov. 10, 1988, now abandoned.

This invention relates to pesticidal compounds, processes for their preparation, compositions containing them and to their use in the treatment of pests. More particularly, the present invention relates to lipid amide pesticides.

European Patent publications 143593 and 225011 discloses inter alia pesticidal compounds where a polynuclear carbocyclic or heterocyclic fused ring system containing at least one aromatic ring is substituted by an alkyl or alkoxy side chain which terminate in a dienamide moiety. No nitrogen-containing heterocycles are exemplified or mentioned.

It has now been discovered that compounds having a nitrogen containing heterocyclic ring system attached to an alkyl or alkoxy side chain which terminates in an enamide or dienamide moiety have interesting pesticidal properties.

Accordingly, the present invention provides a compound of the formula (I):

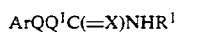

$$ArQQ^1C(=X)NHR^1 \qquad (I)$$

or a salt thereof, wherein Ar is an optionally substituted polycyclic ring system containing n rings, where n is the integer 2 or 3, at least n-1 rings being aromatic and containing one to three ring nitrogen atoms and optionally containing additional heteroatoms; Q is an alkyl chain containing 1 to 12 carbon atoms and optionally containing a sulphur or one or two oxygen atoms; $Q^1$ is a group $(C(R^2)=C(R^3))_a—(C(R^4)=C(R^5))$ wherein a hydrogen and the other two being independently selected from hydrogen, halo, $C_{1-4}$ alkyl or $C_{1-4}$ haloalkyl; X is oxygen or sulphur; and $R^1$ is selected from hydrogen and $C_{1-8}$ hydrocarbyl optionally substituted by dioxalanyl, halo, cyano, trifluoromethyl, trifluoromethylthio or $C_{1-6}$ alkoxy.

Suitable substituents for the polycyclic ring system Ar include halo, cyano and $C_{1-6}$ alkyl and $C_{1-6}$ alkoxy each optionally substituted by one to five halos or the substituent is a group $S(O)_mR^6$ wherein m is 0, 1 or 2 and $R^6$ is $C_{1-6}$ alkyl optionally substituted by halo. The Ar ring system will normally contain up to three substituents and suitably one or two substituents such as alkyl, halo or $CF_3$. The substitution of the Ar ring systems will depend on the nature of this ring system but it is often convenient for Ar to be unsubstituted.

Preferably any additional ring heteroatom is sulphur. Preferably there is only one ring nitrogen. Preferably a ring nitrogen is adjacent either to a second ring nitrogen, a quaternary or substituted ring carbon. Suitably the Ar ring system contains two rings. Suitable examples of such ring systems include quinoline, isoquinoline, quinoxaline, cinnoline, quinazoline, phthalazine, benzothiazole, naphthyridine, tetrahydroquinoline and tetrahydroisoquinoline; quinoline is preferred.

The alkyl chain Q may be attached at any position of the Ar ring system. However it will preferably be attached at a carbon atom which is adjacent to a ring nitrogen.

When Q contains an oxygen or sulphur atom, this is not normally at the end of the alkyl chain adjacent to $Q^1$. The sulphur atom may be present as the sulphone or sulphoxide if desired. Suitably Q contains 1 to 8 carbon atoms and, optionally, one oxygen atom. When Q contains one oxygen atom or a sulphur atom, this is conveniently at the end of the alkyl chain adjacent to the Ar ring system. When Q contains two oxygen atoms, these are not normally adjacent. Q is preferably an $O(CH_2)_7$ group, the oxygen being adjacent to Ar.

In $Q^1$ the carbon atom substituted by $R^5$ is adjacent to the $C(=X)NHR^1$ moiety.

Preferably a is 1 and $R^2$, $R^3$, $R^4$ and $R^5$ are chosen from hydrogen, halo and methyl. Preferably $R^3$ and $R^5$ are hydrogen and $R^4$ is hydrogen, fluoro or methyl and $R^2$ is hydrogen or fluoro.

Preferably the stereochemistry of all double bonds is trans (E)

Preferably X is oxygen.

Suitably $R^1$ is $C_{1-6}$ alkyl optionally substituted by dioxalanyl or $R^1$ is $C_{2-5}$ alkenyl. Most suitably $R^1$ is a branched chain $C_{4-6}$ alkyl group, such as isobutyl, 1,2-dimethylpropyl, 1,1,2-trimethylpropyl, 2,2-dimethylpropyl, or $R^1$ is 2-methyl-prop-2-enyl or 2-methyl-1,3-dioxalan-2-yl. Preferably $R^1$ is isobutyl or 2-methyl-prop-2-enyl when $R^2$, $R^3$ and $R^5$ are hydrogen and $R^4$ is methyl.

One group of compounds of the present invention includes those of the formula (II):

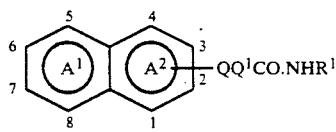

wherein one of the rings $A^1$, $A^2$ is an aromatic ring containing a nitrogen atom and optionally substituted as hereinbefore defined and the other is a $C_6$-carbocyclic aromatic ring, the side chain is attached at position 1 or 2 and Q, $Q^1$ and $R^1$ are as hereinbefore defined. Suitably Q is or $O(CH_2)_{4-9}$. Suitable $Q^1$ is $CH=CR^3—CR^4=CR^5$ and $R^4$ is hydrogen or methyl, and $R^3$ and $R^5$ are hydrogen or fluoro.

One preferred group of compounds of the present invention includes those of the formula (III):

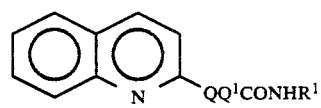

or a salt thereof wherein Q, $Q^1$, and $R^1$ are as hereinbefore defined. Suitably Q and $Q^1$ form a group $—OQ^3CH=CR^3—CR^4=CR^5—$ wherein $Q^3$ is $C_{1-8}$ alkyl group, $R^4$ is hydrogen or methyl and $R^3$ and $R^5$ are hydrogen or fluoro. Suitably $Q^3$ is $(CH_2)_7$ Preferred compounds include:

- (2E,4E/2Z,4E)N-Isobutyl-3-methyl-12-(2-quinolinyloxy)-dodeca-2,4-dienamide
- (2E,4E) N-Isobutyl 12-(2-quinolinoxy)-dodeca-2,4-dienamide (2E,4E) N-Isobutyl 3-methyl-12-(2-quinolinoxy)-dodeca-2,4-dienamide
- (2E,4E) N-1,1,2-Trimethylpropyl 12-(2-quinolinyloxy)-dodeca-2,4-dienamide
- (2E,4E) N-2,2-Dimethylpropyl 12-(2-quinolinyloxy)-dodeca-2,4-dienamide (2E,4E) N-(2-Methyl-1,3-dioxolan-2-yl)methyl 12-(2-quinolinyloxy)-dodeca-2,4-dienamide
(2E,4E) N-1,2-dimethylpropyl 12-(2-quinolinyloxy)-dodeca-2,4-dienamide
(2E/Z,4E) N-2-Methyl-prop-2-enyl 3-methyl-12-(2-quinolinyloxy)-dodeca-2,4-dienamide
(2Z,4E)N-Isobutyl-2-fluoro-3-methyl-12-(2-quinolinyloxy)dodeca-2,4-dienamide
(2E,4Z)N-Isobutyl 4-fluoro-12-(2-quinolinyloxy)-dodeca-2,4-dienamide
(2E,4Z)N-Isobutyl 4-fluoro-3-methyl-12-(2-quinolinyloxy)dodeca-2,4-dienamide
(2E/Z,4E) N-1-Methylpropyl 3-methyl-12-(2-quinolinyloxy)-dodeca-2,4-dienamide
(2E,4E) N-Isobutyl 12-(4-methyl-2-quinolinyloxy)-dodeca-2,4-dienamide
(2E/Z,4E) N-Isobutyl 3-methyl-12-(4-methyl-2-quinolinyloxy)-dodeca-2,4-dienamide
(2E/Z,4E) N-2-Methylprop-2-enyl 3-methyl-12-(4-methyl-2-quinolinyloxy) dodeca-2,4-dienamide
(2E,4E) N-1,2-dimethylpropyl 12-(4-methyl-2-quinolinyloxy)-dodeca-2,4-dienamide
(2E/Z,4E) N-Isobutyl 3-methyl-12-(4-chloro-2-quinolinyloxy)-dodeca-2,4-dienamide
(2E,4E) N-Isobutyl 12-(4-chloro-2-quinolinyloxy)-dodeca-2,4-dienamide
(2E,4E) N-Isobutyl 3-methyl-12-(4-trifluoromethyl-2-quinolinyloxy)-dodeca-2,4-dienamide
(2E/Z,4E) N-Isobutyl 3-methyl-12-(6-bromo-2-quinolinyloxy)-dodeca-2,4-dienamide
(2E,4E) N-Isobutyl 12-(6-bromo-2-quinolinyloxy)-dodeca-2,4-dienamide
(2E/Z,4E) N-Isobutyl 3-methyl-12-(6-iodo-2-quinolinyloxy)-dodeca-2,4-dienamide
(2E/Z,4E) N-Isobutyl 3-methyl-12-(6-fluoro-2-quinolinyloxy)-dodeca-2,4-dienamide
(2E/Z,4E) N-Isobutyl 3-methyl-12-(3-bromo-2-quinolinyloxy)-dodeca-2,4-dienamide
(2E/Z,4E) N-Isobutyl 3-methyl-12-(3-fluoro-2-quinolinyloxy)-dodeca-2,4-dienamide
(2E/Z,4E) N-Isobutyl 3-methyl-12-(8-fluoro-2-quinolinyloxy)-dodeca-2,4-dienamide
(2E,4E) N-Isobutyl 12-(6-chloro-2-quinolinyloxy)-dodeca-2,4-dienamide
(2E/Z,4E) N-Isobutyl 3-methyl-12-(6-chloro-2-quinolinyloxy)-dodeca-2,4-dienamide
(2E,4E) N-Isobutyl 12-(6-trifluoromethyl-2-quinolinyloxy) dodeca-2,4-dienamide
(2E/Z,4E) N-Isobutyl 3-methyl-12-(6-trifluoromethyl-2-quinolinyloxy)dodeca-2,4-dienamide
(2E/Z,4E) N-Isobutyl 3-methyl-12-(3-chloro-2-quinolinyloxy) dodeca-2,4-dienamide
(2E/Z,4E) N-Isobutyl 3-methyl-12-(4-methoxy-2-quinolinyloxy) dodeca-2,4-dienamide
(2E/Z,4E) N-Isobutyl 3-methyl-12-(3-cyano-2-quinolinyloxy) dodeca-2,4-dienamide
(2E/Z,4E) N-Isobutyl 3-methyl-12-(3-nitro-2-quinolinyloxy) dodeca-2,4-dienamide
(2E/Z,4E) N-Isobutyl 3-methyl-12-(8-chloro-2-quinolinyloxy) dodeca-2,4-dienamide Salts of the compounds of the present invention will normally be acid addition salts. Such salts may be formed from mineral or organic acids.

Preferred salts includes those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methanesulphonic, ethanesulphonic, benzenesulphonic, toluene-p-sulphonic, lactobionic, glucuronic, thiocyanic, propionic, embonic, naphthenoic and perchloric acids.

The compounds of formula (I) may exist in a number of stereoisomeric forms. The present invention encompasses both individual geometric and stereoisomers and mixtures thereof. The present invention also encompasses compounds of the formula (I) containing radioisotopes, particularly those in which one to three hydrogen atoms are replaced by tritium or one or more carbon atoms are replaced by $^{14}C$.

In a further aspect, the present invention provides a process for the preparation of a compound of the formula (I) as hereinbefore defined which comprises:

(a) when it is required to prepare a compound of the formula (I) wherein X is oxygen, the reaction of the corresponding acid or acid derivative $ArQQ^1COZ^1$ with an amine $H_2NR^1$ wherein $Ar,Q,Q^1$ and $R^1$ are as hereinbefore defined and $Z^1$ is hydroxy, $C_{1-6}$ alkoxy, halo or a phosphoroimidate ester ($-P(\rightarrow O)(O-aryl)NH$—aryl where aryl is $C_{6-10}$ aryl)

(b) The formulation of the $Q^1$ moiety through a Wittig type reaction.

(c) the conversion of one compound of the formula (I) into another compound of the formula (I) by methods well known to those skilled in the art.

Process (a) is normally carried out at a non-extreme temperature, for example between $-25°$ and $150°$ C. in an anhydrous aprotic solvent, such as ether, dichloromethane, toluene or benzene. The precise conditions will be dependent on the nature of the group $Z^1$, for example when $Z^1$ is alkoxy the reaction is conveniently carried out at an elevated temperature, i.e. $50°$ to $125°$ C., and conveniently at reflux preferably in the presence of a trialkyaluminium compound, such as trimethylaluminium, which forms a complex with the amine $H_2NR^1$. When $Z^1$ is halo or phosphoroimidate the reaction is conveniently carried out at $0°$ to $30°$ C. and suitably at room temperature preferably in the presence of a tertiary amine, such as triethylamine.

If the acid derivative is an acid halide, for example the acid chloride, then it may be formed from the corresponding acid by reaction with a suitable reagent such as oxalyl chloride or thionyl chloride. When $Z^1$ is a phosphoroimidate group then this is suitably formed from $(PhO)P(\rightarrow O)NHPhCl$ where Ph is phenyl. The acid, or the acid function in the compound $ArQQ^1COZ^1$, may be prepared by hydrolysis of the corresponding ester.

The esters may be prepared by a number of alternative routes, for example:

(i) a conventional Wittig or Wadsworth-Emmons reaction, using for example an aldehyde and ethoxycarbonylmethylene triphenylphosphorane or an anion from triethylphosphonocrotonate or 3-methyl triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques. The Wittig-type reagent may be produced for example by the following route or a modification thereof:

-continued

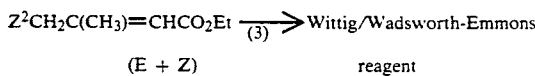

Wherein: $Z^2 = (\text{aryl})_3 P-$ or $(O\text{-alkyl})_2 P(=O)-$, preferably aryl is phenyl and alkyl is ethyl
(1) N-bromo succinimide
(2) e.g. $(EtO)_3P$ or $(Ph)_3P$
(3) This reaction is normally carried out in the presence of a base such as lithium diisopropylamide, butyllithium, sodium alkoxide or sodium hydride.

(ii) by rearrangement and elimination of $HS(\to O)Z^3$ from a compound of formula:

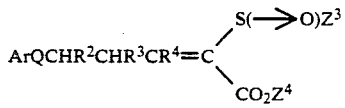

wherein Ar, Q, $R^2$, $R^3$ and $R^4$ are as hereinbefore defined, $Z^3$ is any suitable group, such as phenyl, $Z^4$ is $C_{1-4}$ alkyl, e.g. methyl or ethyl.

The above compound may be obtained by reaction of a compound $ArQCHR^2CHR^3CR^4O$ with a compound $Z^3S(O)CH_2CO_2Z^4$.

(iii) By elimination on a compound $ArQCHR^2CR^3(OZ^5)CR^4=CR^5CO_2Z^4$ wherein Ar, Q, $R^2$, $R^3$, $R^4$, $R^5$ and $Z^4$ are as defined above, and $Z^5$ is H or $C_{1-4}$ acyl such as acetyl. The reaction is preferably carried out in an aromatic solvent, conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $ArQCR^2=CR^3C(=O)R^4$ with one of formula $Me_3SiCHR^5CO_2Z^4$, wherein Ar, $R^2$ to $R^5$, Q and $Z^4$ are as hereinbefore defined.

This process may be carried out in an anhydrous solvent, e.g. tetrahydrofuran in the absence of oxygen, in the presence of a base, e.g. lithium cyclohexylisopropylamide.

(v) by reaction of compound of formula $ArQCR^2=CR^3C(OZ^6)=CR^5CO_2Z^4$ with a compound of formula $R^4M^1$ wherein Ar, Q, $R^2$, $R^3$, $R^4$, $R^5$ and $Z^4$ are as hereinbefore defined, $Z^6$ is a suitable group such as dialkylphosphate or trifluoromethanesulphonate and $M^1$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxygen.

(v) by reaction of a compound of formula $ArQCR^2=CR^3M^2$ with one of formula $halCR^4=CR^5CO_2Z^4$, wherein Ar, Q, $R^2$, $R^3$, $R^4$, $R^5$ and $Z^4$ are as hereinbefore defined, hal is halo and $M^2$ is a silyl or metal containing group, such as trimethylsilyl or a group containing zirconium, aluminum or zinc, for example a bis(cyclopentadienyl)zirconium chloride group. This process is normally carried out at a non-extreme temperature i.e. between 0° and 100° C. and conveniently at room temperature, in a non-aqueous ethereal solvent such as tetrahydrofuran, in the presence of a palladium (O) catalyst, (such as bis(triphenylphosphine)palladium) and under an inert atmosphere of nitrogen or argon.

(vii) by elimination of $Z^7S(\to O)H$ from a compound of formula

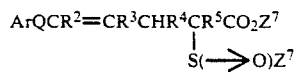

wherein $R^2$, $R^3$, $R^4$ and $R^5$ are as hereinbefore defined, and $Z^7$ is alkyl or substituted phenyl, for example, methyl or 4-chlorophenyl.

The above compound may be obtained by reaction of a compound $ArQCHR^2CR^3=CHR^4$ with $Z^7S(O)CH_2CO_2Z^4$.

Process (b) may be carried out by having an aldehyde or ketone group attached either to the amide end or to the ArQ fragment of the compound of formula (I) and then reacting this with the appropriate phosphorous ylid, i.e.: $ArQ(CR^2=CR^3)_a COR^7 + Z^8CR^8(CR^4=CR^5)_d CONHR^1$ (See Scheme 1) or $ArQ(CR^2=CR^3)_a C(R^7)=Z^8 + R^8CO (CR^4=CR^5)_d CONHR$ wherein Ar, Q, a, $R^1$, $R^2$, $R^3$, $R^4$ and $R^5$ are as hereinbefore defined, d is 0 or 1 and $a+d$ is 0 or 1, $R^7$ is $R^2$ or $R^4$ and $R^8$ is $R^3$ or $R^5$, and $Z^8$ is an appropriately substituted phosphorous residue.

Process (b) is carried out in an anhydrous inert solvent, for example an ether such as tetrahydrofuran, optionally in the presence of a base, and preferably in the absence of oxygen, e.g. under a nitrogen atmosphere, at a low temperature ($-60°$ to $20°$ C.). The phosphorous ylid is conveniently a Wittig or Wadsworth Emmons reagent, i.e. $Z^8$ is a group $(Z^9)_3P$ or $(Z^{10})_2P=O$ wherein $Z^9$ is a $C_{1-4}$ alkyl or $C_{6-10}$ aryl, preferably phenyl, group and $Z^{10}$ is a $C_{1-4}$ alkoxy, preferably ethoxy, group. The phosphorous ylid may be obtained from its precursor as described above by reaction with a base such as lithium diisopropylamide, butyllithium, sodium alkoxide or sodium hydride.

Compounds of the formula (I) wherein X is sulphur are preferably prepared by process (b) when $Z^8$ is a group $(Z^{10})_2P=O$ as hereinbefore defined under the conditions described above.

The aldehyde intermediates $ArQ(CR^2=CR^3)_a CH=O$ may be prepared by acid hydrolysis of a ketal or acetal in a solvent such as acetone-water or by oxidation of the appropriate alcohols using for example pyridinium chlorochromate, pyridinium dichromate or oxalyl chloride-dimethyl sulphoxide in a solvent such as dichloromethane. The aldehydes may also be prepared by reduction of the appropriate nitriles with a reagent such as diisobutylaluminium hydride in hexane.

In some cases the aldehydes are conveniently prepared by ozonolysis of a compound $ArQCH=CH_2$ in a solvent such as dichloromethane at low temperature with subsequent destruction of the ozonide with dimethyl sulphide or triphenyl phosphine.

In some cases aldehydes are conveniently prepared by deprotection under acid conditions of a compound such as $ArQ^1CH=CHOMe$, the latter being prepared by Wittig reaction of a compound $ArQ^1CH=O$ with $Ph_3P=CHOMe$, where Ph is phenyl under conditions described previously.

The alcohols $ArQCHR^2OH$ (Scheme 3 and 4) may be prepared by (a) Reaction of $ArOM^3$ with $LQ^2CHR^2OH$ where $M^3$ is an alkali metal such as sodium and L a leaving group such as halogen or mesylate in an aprotic solvent such as dimethylformamide and $Q^2$ and O combine to form Q.

(b) Reaction of ArOH with $LQ^2CHR^2OL^1$ where $L^1$ is a group such a tetrahydropyranyl under phase transfer conditions, for example 50% aqueous sodium hydroxide and tetrabutylammonium bromide at 90°. This may be followed be deprotection under acidic conditions.

(c) Reaction of ArOH, with $HOQ^2CHR^2OH$ in the presence of a dehydrating agent, such dicyclohexylcarbodiimide, followed by deprotection.

(d) Reaction of $ArL^2$, where $L^2$ is a leaving group such as halo, with $M^3OQ^2CHR^2OL$ where $L^3$ is hydrogen or tetrahydropyranyl. This route is particularly applicable to systems where $L^2$ is activated by a heteroatom.

(e) Reaction of $ArCH_2L^2$ with a compound $MOQ^3CHR^2OL^3$ by analogy with (d) where $Q^5$, O and $CH_2$ combine to form Q.

(f) By reduction of an ester $ArQCO_2Z^4$, or of the appropriate carboxylic acid by for instance lithium aluminium hydride or diborane in a solvent such as tetrahydrofuran or diisobutylaluminium hydride in hexane-dichloromethane.

(g) By reaction of a compound $ArL^2$, with a compound $HC{\equiv}C{-}Q^4{-}OH$, where $Q^4$ is a polymethylene chain, in the presence of a palladium catalyst, such as bistriphenylphosphine palladium dichloride-cuprous iodide, followed by complete hydrogenation of the triple bond.

(h) By reaction of a compound $ArCH_2M^3$ with a compound $LQ^2CHR^2OL^1$ where $Q^2$ and $CH_2$ combine to form Q.

(i) By hydrolysis of a compound $ArOQ^5OQ^6CHR^2OAc$ prepared from $ArOQ^5OQ^6CHR^2L^3$ prepared by reaction of $ArOQ^5OH$ with a compound $L^4Q^6CHR^2L^3$ where $L^3$ and $L^4$ are halogen, e.g. chlorine or bromine and $Q^5$, $Q^6$ and two oxygens combine to form Q.

The intermediates $ArQCH^2{=}CR^3C(R^4)O$ may be prepared from the appropriate alcohols by analogy with previously described methods. The alcohols $ArQCR^2{=}CR^3CH(R^4)OH$ may be prepared by reaction of $ArQCR^2{=}CR^3CHO$ with a Grignard reagent $R^4Mghal$.

The intermediates $ArSQ^2CH_2OH$ may be prepared by reacting a compound $ArSM^3$, with $LQ^2CH_2OH$ in a solvent such as ethanol, dimethylformamide or toluene.

The attached reaction schemes assist in illustrating the preparation of the intermediates and their conversion to compounds of the formula (I).

The intermediates of the present invention form a further aspect of the prevent invention and may be prepared where appropriate by standard methods other than those described.

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of h igh volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops in in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella, Culex spp. Tribolium castaneum, Sitophilus granarius, Periplaneta amiercana* and *Blattella germanica.* The compounds of formula (I) are thus useful in the control of arthropods, e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Lirimyza and Melophagus spp.), Phthiraptera (Malophaga e.g. Damalina spp. and Anoplura e.g. Linognathus and Maematopinus spp.), Hemiptera (e.g. Aphis, Bemisia, Phorodon, Aeneolamia, Empoasca, Parkinsiella, Pyrilla, Aonidiella, Coccus, Pseudococus, Helopeltis, Lygus, Dysdercus, Oxycarenus, Nezara, Aleurodes, Triatoma, Psylla, Mysus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),.

Acarine pests include ticks, e.g. members of the genera Boophilus, Ornithodorus, Rhipicephalus, Amlyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); heterodera spp. (e.g. *H. avenae;* Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. r. reniformis); Rotylenchus spp. (e.g. *R. robustus*); Helicotylenchus spp. (e.g. *H. multicinctus*); Hemicycliophora spp. (e.g. H. gracilis); Criconemoides spp. (e.g. *C. similus*); Trichodorus spp. (e.g. *T. primitivus*); dagger nematodes such as Xiphinema spp. (e.g. *X. diversicaudatum*), Longidorus spp. (e.g. L. elongatus); Hopolaimus spp. (e.g. *H. coronatus*); Aphelenchoides spp. (e.g. *A. ritzema-bosi, A. besseyi*); stem and bulb eelworms such as Ditylenchus spp. (e.g. D. dipsaci).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10.1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilisers and as scavengers.

Industrial Applicability

Compounds of the present invention show activity as pesticides.

| Formulations | | |
|---|---|---|
| 1. | Emulsifiable Concentrate | |
| | Compound of formula (I) | 10.00 |
| | Ethylan KEO | 20.00 |
| | Xylene | 67.50 |
| | Butylated Hydroxyanisole | 2.50 |
| | | 100.00 |
| 2. | Wettable Powder | |
| | Compound of formula (I) | 25.00 |
| | Attapulgite | 69.50 |
| | Sodium isopropylbenzene sulphonate | 0.50 |
| | Sodium salt of condensed naphthalene sulphonic acid | 2.50 |
| | Butylated hydroxytoluene | 2.50 |
| | | 100.00 |
| 3. | Dust | |
| | Compound of formula (I) | 0.50 |
| | Butylated Hydroxyanisole | 0.10 |
| | Talc | 99.40 |
| | | 100.00 |
| 4. | Bait | |

| Formulations | |
|---|---|
| Compound of formula (I) | 40.25 |
| Icing Sugar | 59.65 |
| Butylated hydroxy toluene | 0.10 |
| | 100.00 |
| 5. Lacquer | |
| Compound of formula (I) | 0.1 |
| Piperonyl Butoxide | 0.5 |
| Butylated Hydroxyanisole | 10.1 |
| High aromatic white spirit | 92.0 |
| | 100.00 |
| 6. Aerosol | |
| Compound of formula (I) | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound of formula (I) | 0.1 |
| Butylated Hydroxyanisole | 0.1 |
| Xylene | 10.0 |
| Odourless Kerosene | 89.8 |
| | 100.00 |
| 8. Potentiated Spray | |
| Compound of formula (I) | 0.1 |
| Piperonyl Butoxide | 0.5 |
| Butylated Hydroxyanisole | 0.1 |
| Xylene | 10.1 |
| Odourless Kerosene | 89.2 |
| | 100.00 |

The following Examples illustrate, in a non-limiting manner, preferred aspects of the invention.

EXPERIMENTAL

General Synthetic Methods and Procedures

Various compounds were synthesized and characterized in accordance with the following experimental procedures.

$^1$H N.m.r. spectra were obtained on a Bruker AM-250 spectrometer in dueterochloroform solutions with tetramethylsilane as internal standard and are expressed as ppm from TMS, number of protons, number of peaks, coupling constant J Hz.

Progress of reactions could also be conveniently monitored on plastic sheets (40×80 mm) precoated with 0.25 mm layers of silica gel with fluoroscent indicator and developed in appropriate solvent or solvent mixture. Temperatures are in degrees Celsius throughout.

Conventional work up was performed as follows:

The reaction mixture was partitioned between an organic solvent and water. The phases were separated and the organic phase washed with at least an equivalent volume of dilute aqueous base as appropriate, and then with a saturated brine wash. The organic phase was then dried over a drying agent, suitably magnesium sulphate, and filtered. The volatile solvents were removed and the resulting product subjected to the appropriate purification and used in the next stage of synthesis or analysed as the final product.

EXAMPLE I

The Method of Stages a–c below was similarly applied for all compounds of formula (I) using modifications as indicated in the following Examples.

Compound 1 (2E/Z,4E) N-Isobutyl 3-methyl-12-(2-quinolinyloxy)-dodeca-2,4-dienamide Stage a, 8-(2-quinolinyloxy)octan-1-ol (i) Sodium hydride (67 mmol) was added to 2-hydroxyquinoline (67 mmol) in dry dimethylformamide. After 1 hour at room-temperature 8-bromooctan-1-ol (67 mmol) (Kang et al, Synthesis, 1985, 1161) was added. After 18 hours at room-temperature the mixture was diluted with water and extracted with ether. The ethereal solution was washed with dilute hydrochloric acid, sodium bicarbonate, brine, dried over magnesium sulphate and filtered. The solvent was removed under vacuum. After purification upon a silica column with ether-hexane as eluant 8-(2-quinolinyloxy)octan-1-ol was obtained (4.9 g).

or (ii) Sodium metal (1.7 g) was added to 1,8-octanediol (21.9 g) in dry toluene (150 ml) at 100°. The mixture was heated under reflux until all the sodium had been consumed and 2-chloroquinoline (ex Aldrich) (12.3 g) in dry toluene (50 ml) was added. After heating under reflux for about 5 hours the reaction mixture was worked up in conventional fashion and the crude product purified by column chromatography on silica (ether/hexane) to give 8-(2-quinolinyloxy)octan-1-ol as a yellow oil which solidified on standing (10.8 g).

Stage b 8-(2-quinolinyloxy)octan-1-ol

The alcohol (18 mmol) was oxidised under Swern conditions (Dimethyl sulphoxide, 54 mmol; oxalyl chloride, 27 mmol; triethylamine, 90 mmol) in dichloromethane to give 8-(2-quinolinyloxy)octan-1-al which was used directly.

Stage c Ethyl-3-methyl 12-(2-quinolinyloxy)-dodeca-2,4-dienoate

A solution of lithium diisopropylamide in dry tetrahydrofuran prepared from n-butyl lithium (9 mmol) and diisopropylamine (9 mmol) was treated at −60° C. with triethyl 3-methyl-4-phosphonocrotonate (9 mmol) in THF under nitrogen. The mixture was allowed to reach −10° C., cooled to −40° C. and treated with the above aldehyde (9 mmol). After 18 hours at room temperature the mixture was partitioned between ether and water and the ethereal fraction worked up as above. Purification by chromatography (silica; ether/hexane) gave ethyl 3-methyl 12-(2-quinolinyloxy)dodeca-2,4-dienoate.

Stage d (2E/Z,4E) N-Isobutyl 3-methyl 12-(2-quinolinyloxy)dodeca-2,4-dienamide

The ester (1.3 mmol) in dry toluene, was added at −10° C. to a complex prepared from trimethyl aluminium (1.6 mmol) and isobutylamine (1.6 mmol) in dry toluene. The whole was heated under reflux for 5 hours, treated cautiously with 2N-hydrochloric acid, and the organic layer separated and worked-up as above. Chromatography in silica (ether/hexane) gave N-Isobutyl 3-methyl 12-(2-quinolinyloxy)dodeca-2,4-dienamide as a 55:45 mixture of the 2E, 4E: 2Z, 4E isomers (compound 1) (Tlc. silica/ether; $R_f$ 0.230)

NMR $^1$H (ppm from TMS in CDCl$_3$, integral, multiplicity): 6.9–8.0(m, 6 H), 6.04, 7.60(2 m, 2 H) 5.5–5.6(2

H, 3 s), 4.5 (2 H, t), 3.15 (2 H, t), 1.8 (1 H, m), 1.3–2.3 (12 H, m), 0.92 (6 H, d), 2.25 and 1.95 (3 H, 2 s).

EXAMPLE II

Compound 3 (2E,4E) N-Isobutyl 12-(2-quinolinyloxy)dodeca-2,4-dienamide

Prepared from compound 1 by preparative HPLC. Solvent, 80:20 methanol:water (1500 psi at 7 ml/min$^{-1}$ at 38°) on reverse-phase silica (Dupont-Sorbax RP-C8). NMR$^1$H: 6.9–8.05 (m, 6 H, aryl); 6.05 (m, 2 H, H4,5); 5.58 (s, 1 H, H2); 5.5 (bd.s, NH); 4.45 (t, 2 H, H11); 3.15 (2 H, t), 1.8 (1 H, m); 0.92 (6 H, d, isobutyl); 2.25 (s, 3 H, CH$_3$) 1.3–2.3 (m, 12 H, carbon chain).

The following compounds were similarly prepared by the Method of EXAMPLE I using the appropriate amine NH$_2$R$^1$ in Stage d and the appropriate starting materials in place of triethyl 3-methyl-4-phosphonocrotonate in Stage c and 2-hydroxy quinoline or 2-chloroquinoline in Stage as as indicated:

Compound 2 (2E,4E) N-Isobutyl 12-(2-quinolinyloxy)-dodeca-2,4-dienamide

Starting from triethyl 4-phosphonocrotonate.

Compound 4 (2E,4E) N-1,1,2-Trimethylpropyl 12-(2-quinolinyloxy)-dodeca-2,4-dienamide Starting from triethyl 4-phosphonocrotonate and using 1,1,2-trimethylpropylamine (Jacquier, *Bull. Soc. Chim. France*, 1957, p 600)

Compound 5 (2E,4E) N-2,2-Dimethylpropyl 12-(2-quinolinyloxy)-dodeca-2,4-dienamide Starting from triethyl 4-phosphonocrotonate and using 2,2-dimethylpropylamine (ex. Aldrich).

Compound 6 (2E,4E) N-(2-Methyl-1,3-dioxalan-2-yl)methyl 12-(2-quinolinyloxy) dodeca-2,4-dienamide Starting from triethyl 4-phosphonocrotonate and using (2-methyl-1,3-dioxalan-2-yl)methylamine (Zavylov, *Chem Abs*, 88:89117f)

Compund 7 (2E,4E) N-1,2-Dimethylpropyl 12-(2-quinolinyloxy)dodeca-2,4-dienamide Starting from triethyl 4-phosphonocrotonate and using 1,2-dimethylpropylamine.

Compound 8 (2E/Z,4E) N-(2-Methylprop-2-enyl) 3-methyl 12-(2-quinolinyloxy) dodeca-2,4-dienamide Using 1-amino-2-methyl-prop-2-ene (ex Aldrich).

Compound 9 (2E/Z, 4E) N-(1-Methylpropyl 3-methyl 12(2-quinolinyloxy) dodeca-2,4-dienamide Using 1-methylpropylamine.

Compound 10 (2E,4E) N-Isobutyl 12-(4-methyl-2-quinolinyloxy)-dodeca-2,4-dienamide Starting from 2-chloro-4-methylquinoline (Aldrich) and triethyl 4-phosphonocrotonate.

Compound 11 (2E/Z,4E) N-Isobutyl 3-methyl 12-(4-methyl-2-quinolinyloxy)dodeca-2,4-dienamide Starting from 2-chloro 4-methylquinoline.

Compound 12 (2E/Z,4E) N-(2-Methylprop-2-enyl) 3-methyl (12-(4-methyl-2-quinolinyloxy) dodeca-2,4-dienamide Starting from 2-chloro-4-methylquinoline and using 1-amino 2-methyl prop-2-ene.

Compound 13 (2E,4E) N-1,2-dimethylpropyl 12-(4-methyl-2-quinolinyloxy) dodeca-2,4-dienamide Starting from 2-chloro-4-methylquinoline and triethyl 4-phosphonocrotonate and using 1,2-dimethylpropylamine.

EXAMPLE III

Compound 14 (2E/Z,4E) N-Isobutyl 3-methyl-12-(4-chloro-2-quinolinyloxy)dodeca-2,4-dienamide Starting from 2,4-dichloroquinoline.

2,4-Dihydroxyquinoline (Aldrich) 19.4 g and the phosphorous oxychloride (40 ml) were heated together at 100° C. for 3 hours. The reaction mixture was allowed to cool and poured onto ice-water. After neutralisation with solid sodium carbonate to the solid product was collected by filtration and dried in vacuo to give 2,4-dichloroquinoline (20.5 g).

Similarly prepared was:

Compound 15 (2E,4E) N-Isobutyl 12-(4-chloro-2-quinolinyloxy)-dodeca-2,4-dienamide Starting from 2,4-dichloroquinoline (see Compound 14) and triethyl 4-phosphonocrotonate.

EXAMPLE IV

Compound 16 (2E,4E) N-Isobutyl 3-methyl-12-(4-trifluoromethyl-2-quinolinyloxy)-dodeca -2,4-dienamide Starting from 2-chloro-4-trifluoromethyl-quinoline.

Aniline (ex Aldrich) and ethyl trifluoroacetoacetate (ex Lancaster) were reacted together according to Westland *et al, J. Med. Chem.*, 16, 326 (1973), to give 2-hydroxy-4-trifluoromethylquinoline. The latter (2.5 g), was treated for 30 minutes at 90°–100° C. with phosphorous oxychloride (20 ml) and resublimed phosphorous pentachloride (2.45 g). The reaction mixture was allowed to cool and poured onto ice-water and neutralised with aqueous ammonium hydroxide. Extraction into diethyl ether yielded 2-chloro-4-trifluoromethyl quinoline, which after conventional work-up was used directly in Stage a.

EXAMPLE V

Compound 17 (2E/Z,4E) N-Isobutyl 3-methyl-12-(6-bromo-2-quinolinyloxy)dodeca-2,4-dienamide Starting from 6-bromo-2-hydroxyquinoline.

2-Hydroxyquinoline was converted to 6-bromo-2-hydroxyquinoline according to Paolo and Gianlorenzo, *Chem. Abs.*, 63,5602c, (1965).

Similarly prepared was:

Compound 18 (2E,4E) N-Isobutyl 12-(6-bromo-2-quinolinyloxy)-dodeca-2,4-dienamide Starting from 6-bromo-2-hydroxyquinoline (prepared as for Compound 17) and triethyl 4-phosphonocrotonate.

EXAMPLE VI

Compound 19 (2E/Z,4E) N-Isobutyl 3-methyl-12-(6-iodo-2-quinolinyloxy)dodeca-2,4-dienamide Starting from 6-iodo-2-hydroxyquinoline 2-Hydroxyquinoline was iodinated in the presence of silver sulphate according to Campbell and Roberts, EP 0148623 (1985) to give 6-iodo-2-hydroxyquinoline. 2-chloro-6-iodoquinoline was obtained by analogy with Example IV and used in Stage a.

EXAMPLE VII

Compound 20 (2E/Z,4E) N-Isobutyl 3-methyl-12-(6-fluoro-2-quinolinyloxy)dodeca-2,4-dienamide Starting from 2-chloro-6-fluoroquinoline.

4-Fluoroaniline (ex Aldrich) and anhydrous glycerol (ex Fluka) were reacted together in a Skraup reaction according to Sveinbjornsson et al, *J. Org. Chem.*, 16, 1450 (1951) to give 6-fluoroquinoline. The latter (3.82 g) in glacial acetic acid (22 ml) was treated with 30% hydrogen peroxide (7 ml) for 4 hours at 70°–80° C. Additional 30% hydrogen peroxide (7 ml) was added and the mixture kept for 16 hours at 70°–80° C. The solvents were removed at reduced pressure and the residue neutralized with solid sodium carbonate and extracted with chloroform. The organic phase was washed with hexane and dried to give 6-fluoroquinoline-N-oxide (3.13 g). The latter (1 g) was heated under reflux with acetic anhydride (6 ml) in the absence of moisture for 1 hour, the hot mixture treated with water (6 ml), boiled for 1 hour and poured onto fresh ice. After neutralisation with aqueous sodium carbonate the solid product, 2-hydroxy-6-fluoroquinoline, was collected by filtration and dried (0.39 g). 2-chloro-6-fluoroquinoline was obtained by analogy with Example IV and used in Stage a.

EXAMPLE VIII

Compound 21 (2E/Z,4E) N-Isobutyl 3-methyl-12-(3-bromo-2-quinolinyloxy)dodeca-2,4-dienamide Starting from 2-chloro-3-bromoquinoline.

3-Bromoquinoline (ex Lancaster) was treated in analogous fashion to Example VII to give a mixture of 4-hydroxy-3-bromoquinoline and 2-hydroxy-3-bromoquinoline. Washing with cold chloroform and filtration isolated the latter which was converted to 2-chloro-3-bromoquinoline by analogy with Example IV and used in Stage a.

EXAMPLE IX

Compound 22 (2E/Z,4E)-N-Isobutyl 3-methyl-12-(3-fluoro-2-quinolinyloxy)dodeca-2,4-dienamide Starting from 2-chloro-3-fluoroquinoline.

3-Aminoquinoline (ex Fluka) was reacted with sodium nitrite and fluoroboric acid to give a diazonium salt which was converted thermally to 3-fluoroquinoline according to Roe and Hawkins *J. Am. Chem. Soc.*, 71, 1785, (1949). The latter was converted to 2-hydroxy-3-fluoroquinoline by analogy with Example VII and to 2-chloro-3-fluoroquinoline by analogy with Example IV.

EXAMPLE X

Compound 23 (2E/Z,4E)-N-Isobutyl 3-methyl-12-(8-fluoro-2-quinolinyloxy)dodeca-2,4-dienamide Starting from 2-chloro-8-fluoroquinoline A solution of 2-fluoroaniline (ex. Aldrich) (3 g) in pyridine (20 ml) was treated at 0° with 3-ethoxyacryloyl chloride (3.64 g) (Prepared according to Paul et al, U..S. Pat. No. 2,768,174, (1956)). After 30 minutes at 0°–10° the reaction mixture was partitioned between ether and water and worked-up in conventional fashion. Chromatography on silica (ether : hexane, 1:1) gave N-(2-fluorophenyl)-3-ethoxyacrylamide (1 g). The latter was added in portions to conc. sulphuric acid (15 ml) at room temperature. After stirring overnight the mixture was poured onto ice-water. The resultant cream precipitate was collected and dried in vacuo to give 2-hydroxy-8-fluoroquinoline. This was converted to 2-chloro-8-fluoroquinoline by anlogy with Example IV.

Similarly prepared were:

Compound 24 (2E,4E)-N-Isobutyl 12-(6-chloro-2-quinolinyloxy) dodeca-2,4-dienamide Starting from 2,6-dichloroquinoline (prepared as for compound 23 starting from 4-chloroaniline (ex. Aldrich)) and using triethyl 4-phosphonocrotonate.

Compound 25 (2E/Z,4E)N-Isobutyl 3-methyl-12-(6-chloro-2-quinolinyloxy) dodeca-2,4-dienamide Starting from 2,6-dichloroquinoline

Compound 26 (2E,4E)-N-Isobutyl 12-(6-trifluoromethyl-2-quinolinyloxy) dodeca-2,4-dienamide Starting from 2-chloro-6-trifluoromethylquinoline (prepared as for Compound 23 starting from 4-trifluoromethyl aniline (ex. Aldrich)), and using triethyl 4-phosphonocrotonate.

Compound 27 (2E/Z,4E)N-Isobutyl 3-methyl-12-(6-trifluoromethyl-2-quinolinyloxy) dodeca-2,4-dienamide Starting from 2-chloro-6-trifluoromethylquinoline

Compound 32 (2E/Z,4E)-N-Isobutyl 3-methyl-12-(8-chloro-2-quinolinyloxy dodeca-2,4-dienamide Starting from 2,8-dichloroquinoline (prepared as for Compound 23 starting from 2-chloroaniline (ex Aldrich)).

EXAMPLE XI

Compound 28 (2E/Z,4E)-N-Isobutyl 3-methyl-12-(3-chloro-2-quinolinyloxy) dodeca-2,4-dienamide Starting from 2,3-dichloroquinoline (prepared as for Compound 20 starting from 3-chloroquinoline)

Indole (ex Aldrich) was reacted with chloroform and aqueous sodium hydroxide in the presence of triethylbenzyl ammonium chloride to give 3-chloroquinoline (cf. Sundo et al, Synthesis, 4, 249 (1976). The latter was converted to 2,3-dichloroquinoline, as for Example VII.

EXAMPLE XII

Compound 29 (2E/Z,4E)-N-Isobutyl 3-methyl-12-(4-methoxy-2-quinolinyloxy) dodeca-2,4-dienamide Starting from 2-chloro-4-methoxyquinoline 2,4-Dichloroquinoline (cf. example 14) (4.4 g), sodium methoxide (5.4 g) and dimethyl formamide (70 ml) were heated together at 70° for 2 hrs. The reaction mixture was partitioned between water and ethyl acetate and worked up in standard fashion. The crude product was purified by column chromatography on silica (10% ether in hexane) to give 2-methoxy-4-chloroquinoline (0.87 g) and 2,4-dimethoxyquinoline (1.8 g). The latter was subjected to aqueous hydrolysis by 6N hydrochloric acid for 3 hrs at reflux temperature to give 2-hydroxy-4-methoxyquinoline. This was converted to 2-chloro-4-methoxyquinoline.

EXAMPLE XIII

Compound 30 (2E,Z4E)-N-Isobutyl 3-methyl-12-(3-cyano-2-quinolinyloxy) dodeca-2,4-dienamide Starting from 2-chloro-3-cyanoquinoline.

2-Aminobenzyl alcohol (ex. Aldrich) (2 g) was oxidised with activated manganese dioxide (2.7 g) in chloroform over 20 hours. After filtration and concentration the crude product was purified by column chromatography on silica (ethyl acetate) to give 2-aminobenzaldehyde (1.9 g) as a dark-red oil which was used directly. The latter in xylene (70 ml) was heated under reflux in a Dean-Stark apparatus with ethyl cyanoacetate (3.7 g) (ex. Aldrich) and piperidine (0.8 ml). Upon cooling the 2-hydroxy-3-cyanoquinoline was collected by filtration, washed with ether, dried and converted to the 2-chloro-3-cyanoquinoline.

Similarly prepared was:

Compound 31 (2E/Z,4E)-N-Isobutyl 3-methyl-12-(3-nitro-2-quinolinyloxy) dodeca-2,4-dienamide Starting from 2-hydroxy-3-nitroquinoline (prepared by analogy with Compound 30, from 2-aminobenzaldehyde reacted with ethyl nitroacetate (ex. Aldrich) in xylene in the presence of piperidine).

EXAMPLE XIV

Compound 23 (2Z,4E)N-Isobutyl 2-fluoro-3-methyl-12-(2-quinolinyloxy)dodeca-2,4-dienamide (i) Ethyl bromofluoroacetate (ex Fluorochem) (25 g) and triethyl phosphite (ex Aldrich) (29 g) were heated together at 140-5° for 6 hours in a vessel equipped with a fractionating column. When all the ethyl bromide had distilled off the residue was distilled to give triethyl 2-fluoro-2-phosphonoacetate (22 g) (bp 98°-108° at 0.8 mm). The latter (20 g) was added dropwise to hexane washed sodium hydride (3.3 g) of 60% dispersion) in dry ether (85 ml). After 3 hours at room temperature and 30 mins under reflux, acetone (6.1 ml) was added and the mixture stirred for 4 days at room temperature under nitrogen. After conventional work up the crude product was distilled to give ethyl 2-fluoro-3-methylbut-2-enoate (4 g) (bp. 60°-2° at 15 mm). (Ref. Machleidt & Wessendorf, Ann. 674, 1, (1964)).

Ethyl 2-fluoro-3-methyl-but-2-enoate (4 g, 27.4 mmol), N-bromosuccinimide (5.36 g, 30 mmol) (ex Aldrich) and benzoyl peroxide (30 mg) were heated together under reflux in tetrachloromethane (60 ml) under illumination from a bright light. After 2 hours the solvent was removed and the residue taken up in hexane, filtered through "celite" and concentrated. Short path distillation gave a mixture of (E) and (Z) ethyl 4-bromo-2-fluoro-3-methylbut-2-enoates (4 g) which was heated under reflux in a Vigreux flask with triethylphosphite (3.82 g, 23.07 mmol) at 140°-150°. After 2 hours the crude product was purified by bulb to bulb distillation to give triethyl 2-fluoro -3-methyl-4-phosphonocrotonate (3.5 g, bp 160°-70° at 0.5 mm).

(ii) Sodium metal (1.7 g) was added to 1,8-octanediol (21.9 g) in dry toluene (150 ml) at 100°. The whole was heated under reflux until all the sodium had been consumed and 2-chloroquinoline (ex Aldrich) (12.3 g) in dry toluene (50 ml) was added. After heating under reflux for circa 5 hours the reaction mixture was worked up in conventional fashion and the crude product purified by column chromatography on silica (ether/hexane) to give 8-(2-quinolinyloxy)octan-1-ol as a yellow oil which solidified on standing (10.8 g).

The above alcohol (723 mg) was oxidised under Swern conditions (dimethyl sulphoxide (450 mg), oxalyl chloride (248 μl), triethylamine (1.58 ml)) in dichloromethane (25 ml) to give 8-(2-quinolinyloxy)octan-1-al. This was used directly in the next stage.

(iii) A solution of lithium diisopropylamide in dry tetrahydrofuran, prepared from diisopropylamine (388 μl) and n-butyl lithium (1.65 ml at 1.6M), was treated at −60° with triethyl 2-fluoro-3-methyl-4-phosphonocrotonate (902 mg) in tetrahydrofuran under nitrogen. The temperature was allowed to reach −10° and then re-cooled to −40° whereupon 8-(2-quinolinyloxy)octan-1-al was added. The reaction was maintained at 5° for 16 hours and worked up in conventional fashion. Chromatography on silica (4:1 hexane:ether) gave (2Z, 4E) ethyl 2-fluoro-3-methyl-12-(2-quinolinyloxy)dodeca-2,4-dienoate (0.7 g).

(iv) The above ester (0.4 g) in dry toluene (2.5 ml) was added at −10° to a complex prepared from trimethylaluminium in toluene (650 μl at 1M) and redistilled isobutylamine (135 μl) in toluene (3.5 ml). After heating under reflux for 5 hours the reaction mixture was allowed to cool, treated with 2N hydrochloric acid and stirred for 30 mins. Dilution with ether and conventional work up gave a crude product which was purified by flash column chromatography on silica (1:1 ether:hexane) to give the title compound as a pale yellow oil (180 mg), which gave pale yellow needles on standing.

Compound 34 (2Z,4E) N-(2-methylprop-2-enyl) 2-fluoro-3-methyl-12-(2-quinolinyloxy dodeca-2,4-dienamide Prepared by analogy with Compound 33 except that 1-amino-2-methylprop-2-ene (ex Aldrich) was used instead of isobutylamine in step (iv).

Compound 35 (2Z,4E)N-2,2-Dimethylpropyl 2-fluoro-3-methyl-12-(2-quinolinyloxy) dodeca-2,4-dienamide Prepared by analogy with Compound 33 except that 2,2-dimethylpropylamine (ex. Aldrich) was used in step (iv).

Compound 36

(2Z,4E)N-1,2-Dimethylpropyl 2-fluoro-3-methyl-12-(2-quinolinyloxy) dodeca-2,4-dienamide Prepared by analogy with Compound 33 except that 1,2-dimethylpropylamine (ex. Aldrich) was used in step (iv).

Compound 37

(2Z,4E)N-1-Methylpropyl 2-fluoro-3-methyl-12-(2-quinolinyloxy) dodeca-2,4-dienamide Prepared by analogy with compound 33 except that 1-methylproplamine (ex. Aldrich) was used in step (iv).

Compound 38

(2Z,4E)N-Isobutyl 2-fluoro-3-methyl-12-(4-methyl-2-quinolinyloxy) dodeca-2,4-dienamide Prepared by analogy with compound 33 except that 2-chloro-4-methylquinoline (ex. Aldrich) was used in step (ii).

Compound 39

(2Z,4E)N-Isobutyl 2-fluoro-3-methyl-12-(6-bromo-2-quinolinyloxy) dodeca-2,4-dienamide 2-Hydroxyquinoline (ex. Aldrich) was treated with bromine in acetic acid to give 6-bromo-2-hydroxyquinoline (Paolo and Gianlorenzo, Chem. Abs., 63, 5602C, 1965). The latter was treated with phosphorous oxychloride and phosphorous pentachloride at 90° to give 6-bromo-2-chloroquinoline. The latter was converted to the title compound by analogy with compound 33.

Compound 40

(2Z,4E)N-Isobutyl 2-fluoro-12-(2-quinolinyloxy)-dodeca-2,4-dienamide (i) Methyl trichloracetate (ex. Lancaster) was reacted with antimony trifluoride and bromine according to Niki et al., Chem Lett., 1987, 1149 to give methyl fluorodichloroacetate.

(ii) Activated zinc powder (496 mg), powdered molecular sieve 4A (1.25 g) (ex. BDH) and cuprous chloride (84 mg) were suspended in anhydrous tetrahydrofuran (10 ml). (2E)-10-(2-Quinolinyloxy)dec-2-enal (1 g) was added followed by acetic anhydride (320 μl). The mixture was warmed to 50° under nitrogen and methyl fluorodichloroacetate (328 μl) was added. The mixture was warmed at 50-5° for 4 hours, additional zinc (0.2 g) was added and warming continued for 30 minutes. Upon cooling the reaction mixture was diluted with diethyl ether, filtered through celite and filtrate worked-up in standard fashion. Purification by column chromatography (silica; 4;1, hexane: ether) gave (2Z,4E) methyl 2-fluoro-12-(2-quinolinyloxy)dodeca-2,4-dienoate (0.26 g).

The latter compound was converted to the title compound by analogy with compound 33.

Compound 41

(2Z,4E)N-1,2-Diemethylpropyl 2-fluoro-12-(2-quinolinyloxy) dodeca-2,4-dienamide

Prepared by analogy with Compound 40 except that 1,2-dimethylpropylamine was used in the final stage.

Compound 42

(2Z)N-Isobutyl 2-fluoro-12-(2-quinolinyloxy)dodeca-2-enamide 1,10-Decanediol (ex. Lancaster) was reacted with 2-chloroquinoline, by analogy with compound 33, step (i), to give 10-(2-quinolinyloxy)decan-1-ol. The latter was subjected to Swern oxidation (cf. example XIV) and the aldehyde reacted with ethyl fluoroacetate and diethyl oxalate to give (2Z) ethyl 2-fluoro-12-(2-quinoliny-loxy)dodec-2-enoate. The latter was converted to the title compound by analogy with compound 33, step (iv).

Compound 43

(2Z)N-2-Methylprop-2-enyl 2-fluoro-12-(2-quinolinyloxy)dodeca-2-enamide

Prepared by analogy with Compound 42 using 1-amino-2-methylprop-2-ene in the final stage.

Compound 44

(2Z)N-Isobutyl 2-fluoro-3-methyl-12-(2-quinolinyloxy)dodeca-2-enamide 10-(2-Quinolinyloxy)decan-1-al (cf. Compound 42) was reacted with methyl magnesium iodide and the resultant alcohol subjected to oxidation, by analogy with compound 47, to give 11-(2-quinolinyloxy)undec-2-one. The latter was reacted with the anion derived from lithium diisopropylamide and triethyl 2-fluoro-2-phosphonoacetate (cf. compound 33) to give (2Z) ethyl 2-fluoro-3-methyl-12-(2-quinolinyloxy)dodec-2-enoate.

The latter was converted to the title compound by analogy with compound 33.

Compound 45

(2E,4Z)N-Isobutyl 4-fluoro-12-(2-quinolinyloxy)-dodeca-2,4-dienamide 8-(2-Quinolinyloxy)octan-1-al was prepared as in compound 33 and reacted with diethyl oxalate and ethyl fluoroacetate as in compound 34 to give ethyl 2-fluoro-10-(2-quinolinyloxy)dec-2-enoate. The latter was converted by sequential reduction and oxidation by analogy with compound 34 to give (Z)-2-fluoro-10-(2-quinolinyloxy)dec-2-ene-1-al. This aldehyde was reacted with the anion of N-isobutyl diethylphosphonoacetamide as in compound 34 to give the title compound as a colourless solid.

Compound 46

(2E,4Z)N-1,2-Dimethylpropyl 4-fluoro-12-(2-quinolinyloxy) dodeca-2,4-dienamide (Z)-2-Fluoro-10-(2-quinolinyloxy)dec-2-ene-1al prepared as in compound 45 was treated with the anion derived from lithium diisopropylamide and triethyl phosphonoacetate (ex. Aldrich) in an analogous fashion to compound 33, step (iii), to give (2E,4Z) ethyl 4-fluoro-12-(2-quinolinyloxy-dodeca-2,4-dienamide.

The ester was converted to the title compound by analogy with compound 33.

Compound 47

(2E,4Z)N-Isobutyl 4-fluoro-3-methyl-12-(2-quinolinyloxy) dodeca-2,4-dienamide (Z)-2-Fluoro-10-(2-quinolinyloxy)dec-2-ene-1-al (prepared as for compound 45) (1.2 g) in dry diethyl ether (12 ml) was added to methyl magnesium iodide in dry ether prepared from iodomethane (645 μl) and magnesium (110 mg). After 1.5 hours at room temperature the mixture was treated with satd. aqueous ammonium chloride and worked up in the usual fashion. The crude product was purified by column chromatography (silica; 80:20,ether:hexane) to give (Z)-3-fluoro-11-(2-quinlinyloxy)undec-3-ene-2-ol (1 g).

The above alcohol was oxidised under Sern conditions to give (Z)-3-fluoro-11-(2-quinolinyloxy)undec-3-ene-2-one.

The above ketone was reacted with the anion of N-isobutyl diethylphosphonoacetamide to give the title compound as a wax like solid. tlc (silica; 1:1,ether:hexane):R_f 0.40

Compound 48

(2Z,4Z)N-Isobutyl 2,4-difluoro-12-(2-quinolinyloxy)-dodeca-2,4-dienamide (Z)-2-Fluoro-10-(2-quinolinyloxy)dec-2-ene-1-al, prepared as in compound 45 was reacted with methyl dichlorofluoroacetate as in compound 40 to give (2Z,4Z) methyl 2,4-difluoro-12-(2-quinolinyloxy)dodeca-2,4-dienoate. The latter was converted to the title compound an analogy with compound 33.

Compound 49

(2Z,4Z)N-Isobutyl 2,4-difluoro-3-methyl-12-(2-quinolinyloxy) dodeca-2,4-dienamide (Z)-3-Fluoro-11-(2-quinolinyloxy)undec-3-ene-2-one, prepared as in compound 47 was treated with the anion derived from lithium diisopropylamide and triethyl 2-fluoro-2-phosphonoacetate (cf. compound 33, step (i)) to give ethyl 2,4-difluoro-3-methyl-12-(2-quinolinyloxy) dodeca-2,4-dienoate as a mixture of (2Z,4Z) and (2E,4Z) isomers. The latter was converted to the isomeric amides by analogy with compound 33, purification by column chromatography (silica; ether: hexane, 4:6) afforded the title compound.

TABLE 1

| Compound No. | Ar Substituent | R⁴ | R¹ | Synthetic Method Example |
|---|---|---|---|---|
| 1 (2E/Z) | — | Me | i-Bu | I |
| 2 | — | H | i-Bu | I |
| 3 (2E) | — | Me | i-Bu | II (purified by HPLC from compound 1) |
| 4 | — | H | 1,1,2-trimethyl-propyl | I |
| 5 | — | H | 2,2-dimethyl-propyl | I |
| 6 | — | H | (2-methyl-1,3-dioxalan-2-yl)-methyl | I |
| 7 | — | H | 1,2-dimethyl-propyl | I |
| 8 (2E/Z) | — | Me | 2-methylprop-2-enyl | I |
| 9 (2E/Z) | — | Me | 1-methylpropyl | I |
| 10 | 4-Me | H | i-Bu | I |
| 11 | 4-Me | Me | i-Bu | I |
| 12 (2E/Z) | 4-Me | Me | 2-methylprop-2-enyl | I |
| 13 | 4-Me | H | 1,2-dimethyl-propyl | I |
| 14 (2E/Z) | 4-Cl | Me | i-Bu | III |
| 15 | 4-Cl | H | i-Bu | III |
| 16 | 4-CF₃ | Me | i-Bu | IV |
| 17 (2E/Z) | 6-Br | Me | i-Bu | V |
| 18 | 6-Br | H | i-Bu | V |
| 19 (2E/Z) | 6-I | H | i-Bu | VI |
| 20 (2E/Z) | 6-F | Me | i-Bu | VII |
| 21 (2E/Z) | 3-Br | Me | i-Bu | VIII |
| 22 (2E/Z) | 3-F | Me | i-Bu | IX |
| 23 (2E/Z) | 8-F | Me | i-Bu | X |
| 24 | 6-Cl | H | i-Bu | X |
| 25 (2E/Z) | 6-Cl | Me | i-Bu | I |
| 26 | 6-CF₃ | H | i-Bu | X |
| 27 (2E/Z) | 6-CF₃ | Me | i-Bu | I |
| 28 (2E/Z) | 3-Cl | Me | i-Bu | XI |
| 29 (2E/Z) | 4-OMe | Me | i-Bu | XII |
| 30 (2E/Z) | 3-CN | Me | i-Bu | XIII |
| 31 (2E/Z) | 3-NO₂ | Me | i-Bu | XIII |
| 32 (2E/Z) | 8-Cl | Me | i-Bu | X |

| Compound No. | Ar Substituent | R³ | R⁴ | R⁵ | R¹ | Synthetic method example |
|---|---|---|---|---|---|---|
| 33 (2Z/4E) | — | H | Me | F | i-Bu | XIV |
| 34 (2Z/4E) | — | H | Me | F | 2-methylprop-2-enyl | XIV |
| 35 (2Z/4E) | — | H | Me | F | 2.2-dimethyl-propyl | XIV |
| 36 (2Z/4E) | — | H | Me | F | 1,2-dimethyl-propyl | XIV |
| 37 (2Z/4E) | — | H | Me | F | 1-methylpropyl | XIV |
| 38 (2Z/4E) | 4-Me | H | Me | F | i-Bu | XIV |
| 39 (2Z/4E) | 6-Br | H | Me | F | i-Bu | XIV |
| 40 (2Z/4E) | — | H | H | F | i-Bu | XIV |
| 41 (2Z/4E) | — | H | H | F | 1,2-dimethyl-propyl | XIV |
| 45 (2E/4Z) | — | F | H | H | i-Bu | XIV |
| 46 (2E/4Z) | — | F | H | H | 1,2-dimethyl-propyl | XIV |
| 47 (2E/4Z) | — | F | Me | H | i-Bu | XIV |
| 48 (2Z/4Z) | — | F | H | F | i-Bu | XIV |
| 49 (2Z/4Z) | — | F | Me | F | i-Bu | XIV |

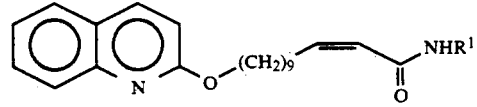

| Compound No. | R⁴ | R⁵ | R¹ | Synthetic method example |
|---|---|---|---|---|
| 42 (2Z) | H | F | i-Bu | XIV |
| 43 (2Z) | H | F | 2-methylprop-2-enyl | XIV |
| 44 (2Z) | Me | F | i-Bu | XIV |

The following compounds were similarly prepared by the Method of EXAMPLE I using the appropriate starting materials in place of 1,8-octanediol in Stage a and the appropriate amine NH₂R¹ in Stage d as indicated:

Compound A2 (2E/Z,4E) N-Isobutyl 3-methyl-11-(2-quinolinyloxy)-undeca-2,4-dienamide

- Starting from 1,7-heptanediol.

Compound A5 (2E,4E)-N-Isobutyl 9-(2-quinolinyloxy) nona-2,4-dienamide

Starting from 1,5-pentanediol and triethyl 4-phosphonocrotonate

Compound A6 (2E,4E)-N-1,2-dimethylpropyl 9-(2-quinolinyloxy) nona-2,4-dienamide

Starting from 1,5-pentanediol and using 1,2-dimethylpropylamine

Compound A7 (2E/Z, 4E)-N-Isobutyl 3-methyl-9-(2-quinolinyloxy)nona-2,4-dienamide Starting from 1,5-pentanediol Compound A8 (2E/Z,4E)-N-(2-Methylprop-2-enyl) 3-methyl-9-(2-quinolinyloxy) -nona-2,4-dienamide Starting from 1,5-pentanediol and using 2-amino 2-methyl prop-2-ene Compound A9 (2E,4E)-N-Isobutyl 10-(2-quinolinyloxy)deca-2,4-dienamide Starting from 1,6-hexanediol and triethyl 4-phosphonocrotonate Compound A10 (2E/Z4E)-N-Isobutyl 3-methyl-10-(2-quinolinyloxy) deca-2,4-dienamide Starting from 1,6-hexanediol Compound A11 (2E/Z,4e)-N-(2-Methylprop-2-enyl)3-methyl-10-(2-quinolinyloxy) deca-2,4-dienamide Starting from 1,6-hexanediol and using 2-amino 2-methyl prop-2-ene

EXAMPLE AI

Compound A1 (2E/Z,4E) N-Isobutyl 3-methyl-11-(2-quinolinylmethoxy)-undeca-2,4-dienamide Starting from 1,7-heptanediol and using the following modified Stage a (ii).

1,7-Heptanediol (ex Lancaster) (1.7 g) was reacted with sodium (0.24 g) in toluene (50 ml) as in Stage A(ii). 2-Chloromethylquinoline hydrochloride (ex Aldrich) was added followed by triethylamine (0.7 ml). After heating under reflux for 6 hours, the reaction mixture was partitioned between water and diethyl ether and the organic phase washed with brine and dried. The crude material was purified by chromatography on silica (eluting with ether-hexane) to give 7-(2-quinolinylmethoxy)heptan-1-ol (0.43 g) which was used in Stage b.

EXAMPLE AII

Compound A3 (2E/Z,4E) N-Isobutyl 3-methyl-11-(2-quinolinylthioxy)undeca-2,4-dienamide Starting from 2-quinolinethiol and using the following modified Stage a.

2-Quinolinethiol (2.86 g) (ex Aldrich) was added to sodium hydride (0.47 g) in toluene. The mixture was warmed to 100° C. and 7-bromo-heptan-1-ol (3.5 g) (Kang et al, Synthesis, 1985, 1161) was added. The reaction mixture was heated at 110° C. for 5 hours, allowed to cool, partitioned between water and diethyl ether and worked up in standard fashion to yield 7-(2-quinolinylthioxy)heptan-1-ol (1.8 g) which was used in Stage b.

EXAMPLE AIII

Compound A4 (2E/Z,4E) N-Isobutyl 12-(2-quinolinyloxy)-dodeca-2,4-dienethioamide

Using the following modified Stage c.

8-(2-Quinolinoxy)octan-1-al was converted to (2E)-10-(2-quinolinyloxy) dec-2-enal and reacted with N-isobutyl 2-(diethoxyphosphonyl)-acetothioamide to give the title compound by methods analogous to those described in EP-209-889 (1987).

EXAMPLE AIV

Compound A12 (2E/Z)-N-Isobutyl 3-methyl-12-(2-quinolinyloxy)dodec-2-enamide

Starting from 2-chloroquinoline and 1,10-decanediol (ex Aldrich) and using the product 10-(2-quinolinyloxy)decan-1-al in the following modified Stage b.

10-(2-Quinolinyloxy)decan-1-al (3.5 g) in dry diethyl ether (15 ml was treated with methyl magnesium iodide in dry ether (2 ml) prepared from magnesium (0.29 g) and iodomethane (0.75 ml). After quenching with satd. aqueous ammonium chloride the reaction was worked-up in the usual manner and the crude product purified by column chromatography on silica (8:2, hexane:ether) to give 11-(2-quinolinyloxy)undecan-2-ol (1.24 g).

The above alcohol was oxidised under Swern conditions (dimethyl sulphoxide, 0.615 g; oxalyl chloride, 0.38 ml; triethylamine, 2.74 ml) to give after column chromatography 11-(2-quinolinyloxy)undecan-2-one (0.96 g).

Lithium N-isopropyl-N-cyclohexylamide was prepared at −78° in anydrous THF from n-butyl lithium (6.1 mmol) and N-isopropyl-N-cyclohexylamine (1.00 ml). Ethyl trimethylsilylacetate (1.1 ml) was added, followed after 10 minutes by addition of the above ketone in THF. The reaction mixture was left at room temperature for 16 hours and worked-up in the usual manner. Excess ethyl trimethylsilylacetate was removed in vacuo and purification by column chromatography on silica (9:1, hexane: ether) gave (2E/Z)ethyl 3-methyl-12-(2-quinolinyloxy)dodec-2-enoate (0.33 g). This was converted to the title compound by analogy with Stages c and d of EXAMPLE I.

EXAMPLE AV

Compound A13 (2E/Z,4E)-N-Isobutyl 3-methyl-13-(2-quinolinyloxy)trideca -2,4-dienamide Starting from 2-methylquinoline, and using the product 9-quinolinylnonan-1-ol in Stages b–d of EXAMPLE I.

3-Methylquinoline (1.5 g) (ex, Aldrich) in THF (25 ml) was treated at −70° C. with n-butyl lithium (10.45 mmol). After 24 hours at −60° 8-bromo-1-tetrahydropyranyloxyoctane (3.06 g) was added. The dark red mixture was kept for 18 hours at −15°, 2 hours at room temperature and worked-up (no acidic washings were employed for the preparation of this example). The crude product was purified on silica (ether : hexane) to give an orange oil. The latter (1.5 g) in methanol (18 ml) was treated with 4-toluenesulphonic acid (2 g) at room temperature for 24 hours. The mixture was diluted with saturated aqueous sodium carbonate and after ether extraction worked-up in conventional manner. Chromatography of the crude material on silica (ether : hexane) gave 9-quinolinylnonan-1-ol (0.7 g).

EXAMPLE AVI

Compound A14 (2E/Z,4E)-N-Isobutyl 3-methyl-13-(2-quinolinyl)trideca-2,4-dienamide.hydrochloride N-Isobutyl 3-methyl-13-(2-quinolinyl)trideca-2,4-dienamide (70 mg) in anhydrous ether (3 ml) was treated with saturated anhydrous hydrogen chloride in ether. The product precipitated out instantaneously. Removal of volatiles in vacuo gave the title compound as a viscous gum.

EXAMPLE AVII

Compound A15 (2E/Z),4E)N-Isobutyl 3-methyl-9-[2-(2-quinolinyloxy)ethoxy]nona-2,4-dienamide Starting from 2-chloroquinoline and using the following modified stage a.

Sodium (322 mg) was reacted with ethanediol (6 ml) with warming, 2-chloroquinoline (2 g) was added and the mixture heated for 5 hours at 90°-95°. The reaction mixture was diluted with water and worked up in standard fasion to give, after chromatography on silica (9:1, ether:hexane), 2-(2-quinolinyloxy)ethanol (1.5 g).

The above alcohol (1.2 g) in anhydrous THF (8 ml) was treated with sodium hydride (95 mg) for 1 hour at room temperature and 30 minutes at 55°. 5-Bromo-1-chloropentane (837 μl) (ex Aldrich) was added and the whole heated under reflux for 6 hours. After cooling and standard work-up the crude product was purified by chromatography on silica (ether:hexane). Traces of starting material were removed in vacuo (0.5 mm at 110°) to give 5-[2-(2-quinolinyloxy)ethoxy]-1-chloropentane. (0.4 g).

The above chloride (0.4 g), dry dimethylformamide (15 ml) and anhydrous sodium acetate (0.69 g) were warmed to 100° and sodium iodide (133 mg) was added. After heating for 10 minutes at 110° the reaction mixture was allowed to cool, diluted with water and worked up in conventional fashion. The resultant acetate (0.4 g) was reacted with potassium hydroxide (0.28 g) in ethanol (4 ml) and water (2 ml) for 1 hour at room temperature. After (ether:hexane) to give 5-[2-(2-quinolinyloxy)ethoxy]-pentan-1-ol (0.29 g).

phosphonocrotonate, and using 1,2-dimethylpropylamine.

Compound B9-(2E, 4E) N-1,2-dimethylpropyl 9(5,7-dibromo-8-quinolinyloxy)-nona-2,4-dienamide Starting from 5,7-dibromo-8-hydroxyquinoline (Lancaster Synthesis), 1,5-pentanediol and triethyl phosphonocrotonate and using 1,2-dimethylpropylamine.

EXAMPLE BI

Compound B1 (2E/Z, 4E) N-Isobutyl 3-methyl-11-(7-chloro-4-quinolinyloxy)undeca-2,4-dienamide Starting from 4-hydroxy-7-chloroquinoline and 1,7-heptanediol.

4,7-Dichloroquinoline (5 g) (ex Aldrich) was heated under reflux with dimethyl sulphoxide (21.5 g), sodium hydroxide (3 g) and water (13.5 ml) for 6 hours. The mixture was poured onto water and made acidic and the product, 4-hydroxy-7-chloroquinoline (3.3 g) was collected by filtration, dried and used in Stage a.

Similarly prepared was:

Compound B10 (2E/Z, 4E)N-Isobutyl

TABLE 1A

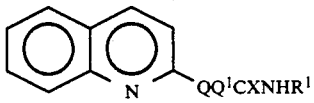

$Q^1 = -(CH=CH)-(CR^4=CH)-$ except where otherwise indicated

| Compound No. | Q | X | R⁴ | R¹ | Synthetic Method Example |
|---|---|---|---|---|---|
| A1 (2E/Z) | CH₂O(CH₂)₆ | O | Me | i-Bu | AI |
| A2 (2E/Z) | O(CH₂)₆ | O | Me | i-Bu | I |
| A3 (2E/Z) | S(CH₂)₆ | O | Me | i-Bu | AII |
| A4 (2E/Z) | O(CH₂)₇ | S | H | i-Bu | AIII |
| A5 | O(CH₂)₄ | O | H | i-Bu | I |
| A6 | O(CH₂)₄ | O | H | 1,2-dimethylpropyl | I |
| A7 (2E/Z) | O(CH₂)₄ | O | Me | i-Bu | I |
| A8 (2E/Z) | O(CH₂)₄ | O | Me | 2-methylprop-2-enyl | I |
| A9 | O(CH₂)₅ | O | H | i-Bu | I |
| A10 (2E/Z) | O(CH₂)₅ | O | Me | i-Bu | I |
| A11 (2E/Z) | O(CH₂)₅ | O | Me | 2-methylprop-2-enyl | I |
| A12 (2E/Z) | O(CH₂)₉ | O | Me | i-Bu | AIV |
| | | | | | $Q^1 = -(CR^4=CH)-$ |
| A13 (2E/Z) | (CH₂)₈ | O | Me | i-Bu | AV |
| A14 (E/Z).HCl | (CH₂)₈ | O | Me | i-Bu | AVI |
| A15 (2E/Z) | O(CH₂)₂O(CH₂)₄ | O | Me | i-Bu | AVII |

The following compounds were similarly prepared by the method of EXAMPLE I using the appropriate starting materials in place of 2-hydroxyquinoline or 2-chloroquinoline and 1,8-octanediol in Stage a and triethyl 3-methyl 4-phosphonocrotonate in Stage c and the appropriate amine NH₂R¹ in Stage d as indicated:

Compound B7 (2E, 4E) N-1,2-dimethylpropyl 9-(8-quinolinyloxy)-nona-2,4-dienamide Starting from 8-hydroxyquinoline (ex Lancaster), 1,5-pentanediol and triethyl phosphonocrotonate, and using 1,2-dimethyl propylamine.

Compound B8 (2E, 4E) N-1,2-dimethylpropyl 9-(3-trifluoromethyl-8-quinolinyloxy)-nona-2,4-dienamide Starting from 3-trifluoromethyl-8-hydroxyquinoline (Lancaster Synthesis), 1,5-pentanediol and triethyl 3-methyl-11-(2-methoxy-4-quinolinyloxy) undeca-2,4-dienamide Starting from 2-methoxy-4-chloroquinoline (prepared as for Compound 29).

EXAMPLE BII

B2 (2E/Z, 4E) N-Isobutyl 3-methyl-11-(2-trifluoromethyl-4-quinolinyloxy)undeca-2,4-dienamide Starting from 2-trifluoromethyl-4-chloroquinoline and 1,7-heptanediol.

Ethyl trifluoroacetoacetate (3.7 g) and aniline (1.8 ml) were reacted together in polyphosphoric acid according to Joullie et al, J. Med. Chem., 16, 134 (1973), to give 2-trifluoromethyl-4-hydroxyquinoline (1.8 g). The latter was reacted with phosphorous oxychloride and phosphorous pentachloride in a similar fashion to Example VIII to give 2-trifluoromethyl-4-chloroquinoline, which was used in Stage a.

EXAMPLE BIII

Compound B3 (2E/Z, 4E) N-Isobutyl 3-methyl-11-(2-chloro-5-quinolinyloxy)undeca-2,4-dienamide Starting from 2-chloro 5-hydroxyquinoline and using the following modified Stage a.

3-Aminocyclohex-2-enone (ex Aldrich) was reacted with methyl propiolate (ex Lancaster) to give 7,8-dihydro-2,5-quinoline-dione according to Speckamp et al *J. Trav. Chem. Pays. bas.*, 91 157 (1972). The latter was converted to 2-chloro-7,8-dihydro-5-quinolinone by analogy with Example VI. The latter compound (2 g) was dissolved in chloroform (200 ml) and treated with bromine (0.53 ml) dropwise at room temperature. After 30 min solid potassium carbonate was added, the mixture was stirred for 1 hour, filtered and solvent removed to give 2-chloro-6-bromo-7,8-dihydro-5-quinolinone (2.86 g). This compound was heated at 110° C. with anhydrous lithium chloride (1.4 g) and dimethylformamide (45 ml) for 3 hours. The mixture was diluted with water, worked-up in conventional fashion and purified by column chromatography on silica (eluting with ether-hexane) to give 2-chloro-5-hydroxyquinoline (0.77 g).

The latter (0.77 g) was reacted with sodium hydride (307 mg) in dimethylformamide (12 ml). After 30 min, 7-bromo-1-(tetrahydropyranyloxy)heptane (1.2 g) was added and after a further 60 hours at room temperature the mixture was diluted with water and worked up in standard fashion. Purification by chromatography on silica (eluting with ether-hexane) gave 1-tetrahydropyranyloxy-7-(2-chloro-5-quinolinyloxy)heptane (0.76 g).

The above compound (0.93 g) in methanol (10 ml) was stirred for 18 hours with Dowex-60W-X8 (1.4 g) (ex BDH), the mixture was filtered, volatile components removed and the residue purified by chromatography on silica (eluting with ether hexane) to give 7-(2-chloro-5-quinolinyloxy)heptan-1-ol (0.2 g), which was used in Stage b.

Compound B4 (2E/Z, 4E) N-Isobutyl 3-methyl-9-(2-chloro-5-quinolinyloxy)-nona-2,4-dienamide Starting from 2-chloro-5-hydroxyquinoline and using 5-bromo-1-tetrahydropyranyloxy)-pentane in the modified Stage a outlined for Compound B3 above, 5-(2-chloro-5-quinolinyloxy)-pentan-1-ol was prepared and used in Stage b.

EXAMPLE BIV

Compound B5 (2E/Z, 4E) N-Isobutyl 3-methyl-11-(2-trifluoromethyl-6-quinolinyloxy)-dodeca-2,4-dienamide Starting from 2-trifluoromethyl 6-hydroxyquinoline and using the following modified Stage a.

Ethyl trifluoroacetoacetate and 4-methoxyaniline were reacted together in presence of polyphosphoric acid to give 2-trifluoromethyl-4-hydroxy-6-methoxyquinoline (cf. Jouillie and Dey). The latter was converted to 2-trifluoromethyl-4-chloro-6-methoxy-quinoline by analogy with Example IV. This was in turn converted first to 2-trifluoromethyl-6-methoxyquinoline by hydrogenation in the presence of palladium on charcoal and thence to 2-trifluoromethyl-6-hydroxyquinoline by reaction with aqueous hydrobromic acid. The latter was reacted with (8-bromo-1-tetrahydropyranyloxy)octane according to Example BIII, 8(2-trifluoromethyl-6-quinolinyloxy)octane-1-ol was prepared and used in Stage b.

Compound B6 (2E/Z,4E)N-(2-Methylprop-2-enyl) 3-methyl-12-(2-trifluoromethyl-6-quinolinyloxy)-dodeca-2,4-dienamide Using 1-amino 2-methyl prop-2-ene.

TABLE 1B

| Compound No. | Quinolinyl Link Position | Ar Substituent | Q | $R^4$ | $R^1$ | Synthetic Method Example |
|---|---|---|---|---|---|---|
| B1 | 4 | 7-Cl | $O(CH_2)_6$ | Me | i-Bu | BI |
| B2 | 4 | 2-$CF_3$ | $O(CH_2)_6$ | Me | i-Bu | BII |
| B3 | 5 | 2-Cl | $O(CH_2)_6$ | Me | i-Bu | BIII |
| B4 | 5 | 2-Cl | $O(CH_2)_4$ | Me | i-Bu | BIII |
| B5 | 6 | 2-$CF_3$ | $O(CH_2)_7$ | Me | i-Bu | BIV |
| B6 | 6 | 2-$CF_3$ | $O(CH_2)_7$ | Me | 2-methyl-prop-2-enyl | BIV |
| B7 | 8 | — | $O(CH_2)_4$ | H | 1,2-dimethylpropyl | I |
| B8 | 8 | 3-$CF_3$ | $O(CH_2)_4$ | H | 1,2-dimethylpropyl | I |
| B9 | 8 | 5,7-diBr | $O(CH_2)_4$ | H | 1,2-dimethylpropyl | I |
| B10 | 4 | 2-OMe | $O(CH_2)_6$ | Me | i-Bu | BI |

The following compounds were similarly prepared by the method of EXAMPLE I using the appropriate starting materials in place of 2-hydroxyquinoline or 2-chloroquinoline and 1,8-octanediol in Stage a as indicated:

Compound C1 (2E/Z, 4E) N-Isobutyl 3-methyl-11-(1-isoquinolinyloxy)undeca-2,4-dienamide Starting from 1,7-heptanediol and 1-hydroxyisoquinoline. (ex Aldrich)

EXAMPLE CI

Compound C2 (2E/Z, 4E) N-Isobutyl 3-methyl-11-(3-chloro-1-isoquinolinyloxy) undeca-2,4-dienamide Starting from 1,7-heptanediol and 1,3-dichloroisoquinoline.

1-Indanone (ex. Aldrich) was treated with amyl nitrite and hydrogen chloride in diethyl ether according to Barrett and Bays GB-966,849(1964) to give 2-isonitroso-indan-1-one. The latter was treated first with phosphorous oxychloride and phosphorous pentachloride and then with hydrogen chloride according to Simchen and Kramer, *Chem. Ber*, 102G, 3666 (1969), to give 1,3-dichloroisoquinoline.

EXAMPLE CII

Compound C3 (2E/Z, 4E) N-Isobutyl 3-methyl-12-(3-isoquinolinyloxy)-dodeca-2,4-dienamide Starting from 3-hydroxy isoquinoline and using a modified Stage a.

Ethyl diethoxyacetate (Ex. Fluka) (25 g) was added to sodium hydroxide (5.68 g) in ethanol (60 ml) and water (30 ml). After heating under reflux for 5 hours the solvents were removed at reduced pressure and the residue dried in vacuo to give sodium diethoxyacetate (23.2 g). The salt was then converted to diethoxyacetyl chloride and reacted with benzylamine to give N-benzyl diethoxyacetamide which was cyclised with conc. sulphuric acid according to Fukumi and Hideshi, *Heterocycles*, 9, 1197 (1978) to give 3-hydroxyisoquinoline.

The latter was treated with sodium hydride and 8-bromo-1-(tetrahydropyranyloxy)octane and the product deprotected with methanol in the presence of "Amberlyst H15" to give 8-(3-isoquinolinyloxy)octan-1-ol.

Similarly prepared were:

Compound C4 (2E/Z, 4E) N-Isobutyl 3-methyl-12-(8-chloro-3-isoquinolinyloxy)dodeca-2,4-dienamide Starting from 3-hydroxyisoquinoline and using the modified Stage a of EXAMPLE II using 2-chlorobenzylamine in place of benzylamine.

Compound C5 (2E/Z)-N-Isobutyl 3-methyl-12-(1-methyl-3-isoquinolinyloxy) dodeca-2,4-dienamide Starting from 3-hydroxy isoquinoline and using α-methylbenzylamine (ex Aldrich) in the modified Stage a of Example C II.

Compound C6 (2E/Z, 4E)-N-Isobutyl 3-methyl-12-(6-chloro-3-isoquinolinyloxy)dodeca-2,4-dienamide Starting from 3-hydroxyisoquinoline and using 4-chlorobenzylamine (ex Aldrich) in the modified Stage a of Example CII.

EXAMPLE CIII

Compound C7 (2E/Z, 4E)-N-Isobutyl 3-methyl-12-(1-chloro-3-isoquinolinyloxy)dodeca-2,4-dienamide Starting from 1-chloro-3-hydroxyquinoline and using the modified Stage a of Example CII 2-Nitrophenylacetic acid (ex Aldrich) (18.1 g) dissolved in 0.1M.aq.sodium hydroxide (100 ml) was subjected to catalytic hydrogenation (at 30–40 psi) over 10% palladium on charcoal (2 g) until uptake ceased. The resultant solution was subjected first to diazotisation and then reaction with sodium cyanide and cuprous cyanide according to Simchen and Hafner, *Ann. Chem.*, 1974, 1802 to give crude 2-cyanophenylacetic acid (14.9 g). The latter was treated with phosphorous pentachloride (20.6 g) and anhydrous hydrogen chloride in di-n-butyl ether (250 ml) for 2 hours. After a further 18 hours the volatiles were removed, the residue washed with water and recrystallized from ethanol to give 1-chloro-3-hydroxy-isoquinoline (1.48 g).

TABLE 1C

Structure: naphthalene-type bicyclic with N at position 2, positions labeled 1,3,4,5,6,7,8; substituent –Q–CH=CH–C(R⁴)=CH–C(=O)–NHR¹

R⁴ = Me, R¹ = i-Bu

| Compound No. | Isoquinolinyl Link Position | Ar Substituent | Q | Synthetic Method Example |
|---|---|---|---|---|
| C1 | 1 | H | O(CH₂)₆ | I |
| C2 | 1 | 3-Cl | O(CH₂)₆ | CI |
| C3 | 3 | H | O(CH₂)₇ | CII |
| C4 | 3 | 8-Cl | O(CH₂)₇ | CII |
| C5 | 3 | 1-Me | O(CH₂)₇ | CII |
| C6 | 3 | 6-Cl | O(CH₂)₇ | CII |
| C7 | 3 | 1-Cl | O(CH₂)₇ | CIII |

The following compounds were similarly prepared by the method of EXAMPLE I using the appropriate starting materials in place of 2-chloroquinoline and 1,8-octanediol in Stage a as indicated:

Compound D1 (2E/Z, 4E) N-Isobutyl 3-methyl-12-(3-chloro-2-quinoxalinyloxy)undeca 2,4-dienamide Starting from 2,3-dichloroquinoxaline (ex. Lancaster).

Compound D2 (2E/Z, 4E) N-Isobutyl 3-methyl-11-(4-chloro-1-phthalazinyloxy)undeca-2,4-dienamide Starting from 1,4-dichlorophthalazine (ex. Lancaster) and 1,7-heptanediol.

Compound D5 (2E/Z, 4E,) N-Isobutyl 3-methyl-12-(2-benzothiazolyloxy dodeca-2,4-dienamide Starting from 2-chlorobenzothiazole (ex Aldrich)

EXAMPLE DI

Compound D3 (2E/Z, 4E) N-Isobutyl 3-methyl-11-(2-chloro-4-quinazolinyloxy)undeca-2,4-dienamide Starting from 1,7-heptanediol and 2,4-dichloroquinazoline.

Benzoyleneurea (ex. Aldrich) was reacted with phosphorous oxychloride in the presense of tri-n-propylamine according to Scarborough et al, *J. Org. Chem.*, 27, 958 (1962) to give 2,4-dichloroquinazoline.

EXAMPLE DII

Compound D4 (2E/Z, 4E) N-isobutyl 3-methyl-12-(3-cinnolinyloxy)-dodeca 2,4-dienamide Starting from 3-hydroxycinnoline and using the following modified Stage a.

Isatin (ex. Aldrich) was hydrolysed with aqueous sodium hydroxide and hydrogenated in the presence of palladium on charcoal, according to Zey,

*J. Het. Chem.*, 9, 1177, (1972), to give sodium 2-aminomandelate which was subjected to first diazotisation and reduction with stannous chloride according to Alford and Schofield, *J. Chem. Soc.* 1952, 2102, subsequent treatment of the tin salt with hydrogen sulphide, neutralisation and purification gave 3-hydroxycinnoline.

3-Hydroxycinnoline (1.5 g) (from which all traces of moisture had been removed by azeotroping with benzene) was stirred at room temperature with sodium hydride (0.25 g) in dry dimethylformamide (20 ml) for 1 hr. 8-Bromooctan-1-ol (2.15 g) was added and the whole heated under reflux for 6 hours. The mixture was diluted with water and worked-up in conventional fashion, the excess solvent was removed in vacuo and the residue purified by chromatography on silica (ethyl acetate-triethylamine) and decolourised over charcoal to give 8-(3-cinnolinyloxy)-octan-1-ol. (1.15 g).

Compound D6 (2Z, 4E) N-Isobutyl 2-fluoro-3-methyl-12-(1,3-benzothiazoyloxy) dodeca-2,4-dienamide Prepared by analogy with compound 33 except that 2-chloro-1,3-benzothiazole (ex. Aldrich) was used in step (ii).

TABLE 1D $$\text{Ar} Q \diagdown \diagup \diagdown \diagup \overset{R^5}{\underset{R^4}{\diagdown}} \diagup \overset{NHR^1}{\underset{O}{\diagdown}}$$

$R^4 = \text{Me}, R^1 = \underline{i}\text{-Bu}$

| Compound No. | Ar | $R^5$ | Ar Substituent | Q | Synthetic Method Example |
|---|---|---|---|---|---|
| D1 | quinoxaline | H | 3-Cl | $O(CH_2)_7$ | I |
| D2 | indazole (N-Me) | H | 4-Cl | $O(CH_2)_6$ | I |
| D3 | indazole (N-Me) | H | 2-Cl | $O(CH_2)_6$ | DI |
| D4 | cinnoline | H | — | $O(CH_2)_7$ | DII |
| D5 | benzothiazole | H | — | $O(CH_2)_7$ | I |
| D6 | benzothiazole | F | — | $O(CH_2)_7$ | XIV |

TABLE II

Characterising data for compounds of formula (I)
Nuclear Magnetic Resonance Data

| Compound No. | Details of Spectrum |
|---|---|
| 1 | 6.9–8.0(m, 6H); 6.04, 7.60(2m, 2H); 5.5–5.6(3s, 2H); 4.50(t, 2H); 3.15(t, 2H); 2.25, 1.95(2s, 3H); 1.8(m, 1H); 1.3–2.3(m, 12H); 0.92(d, 6H). |
| 2. | 7.98, 7.85, 7.72(3d, 3H); 7.63(t, 1H); 7.37(t, 1H); 7.22(m, 1H); 6.90(d, 1H); 6.11(m, 2H); 5.75(d, 1H); 5.46(1H); 4.49(t, 2H); 3.16(t, 2H); 2.17(m, 2H); 1.83, 1.42(2m, 11H); 0.93(d, 6H). |
| 3. | 6.9–8.05(m, 6H); 6.05(m, 2H); 5.58(s, 1H); 5.5(bd.s, 1H) 4.45(t, 2H); 3.15(t, 2H); 2.25(s, 3H); 1.8(m, 1H); 1.3–2.3(m, 12H); 0.92(d, 6H). |
| 4. | 8.08, 7.91, 7.80, 6.96(4d, 4H); 7.70(t, 1H); 7.45(t, 1H); 7.20(m, 1H); 6.17(m, 2H); 5.79(d, 1H); 5.26(s, 1H); 4.57(t, 2H); 2.45(m, 1H); 2.23(m, 2H); 1.90(m, 2H); 1.50(m, 8H); 1.49(s, 6H); 0.96(d, 6H). |
| 5 | 7.99, 7.82, 7.73, 6.99(4d, 4H); 7.62(t, 1H); 7.49(t, 1H); 7.24(m, 1H); 6.12(m, 2H); 5.80(d, 1H); 5.53(t, 1H); 4.46(t, 2H); 3.42(t, 2H); 3.17(d, 2H); 2.20(m, 2H); 1.83(m, 2H); 1.40(m, 8H); 0.93(s, 9H). |
| 6. | 8.00, 7.83, 7.71, 6.90(4d, 4H); 7.62(t, 1H); 7.37(t, 1H); 7.19(m, 1H); 6.12(m, 2H); 5.76(d, 1H); 5.65(t, 1H); 4.48(t, 2H); 3.97(s, 4H); 3.50(d, 2H); 2.18(m, 2H); 1.84(m, 2H); 1.41(m, 8H) 1.33(s, 3H). |
| 7. | 7.97, 7.82, 7.72, 6.91(4d, 4H); 7.61(t, 1H); 7.37(t, 1H); 7.20(m, 1H); 6.13(m, 2H); 5.74(d, 1H); 5.27(d, 1H); 4.48(t, 2H) 3.99(m, 1H); 2.15(m, 2H); 1.82(m, 2H); 1.72(m, 1H); 1.46(m, 8H); 1.11(d, 3H); 0.90(d, 6H). |
| 8. | 8.00, 7.85, 7.72, 6.90(4d, 4H); 7.64(t,1H); 7.38(t, 1H); 6.07, 7.64(m, 2H); 5.62(s, 1H); 5.58, 5.53(2s, H); 4.84(s, 2H); 4.46(t, 2H); 3.88(d, 2H); 2.29, 1.96(2s, 3H); 2.20(m, 2H); 1.83(m, 2H); 1.79, 1.74(2s, 3H); 1.48(m, 8H). |
| 9. | 7.99, 7.85, 7.70, 6.90(4d, 4H); 7.60(t, 1H); 7.37(t, 1H); 6.02, 7.60(m, 2H); 5.57, 5.46(2s, 1H); 5.28(s, 1H); 4.43(t, 2H); 3.96(m, 1H); 2.26, 1.92(2s, 3H); 2.18(m, 2H); 1.87(m, 2H); 1.45(m, 8H); 1.12(d, 3H); 0.94(t, 3H). |
| 10 | 7.90, 7.87(2d, 2H); 7.65, 7.40(2t, 2H); 6.78(s, 1H); 7.22(m, 1H); 6.13(m. 2H); 5.76(d, 1H); 5.50(t, 1H); 4.45(t, 2H); 3.16(t, 2H); 2.62(s, 3H); 2.17(m, 2H); 1.80(m, 3H); 1.42(m, 8H); 0.93(d, 6H). |
| 11. | 7.86, 7.82(2d, 2H); 7.63, 7.40(2t, 2H); 6.76(s, 1H); 6.03, 7.60(m, 2H); 5.59, 5.50(2s, 1H); 5.57(s, 1H); 4.45(t, 2H); 3.12(t, 2H); 2.62(s. 3H); 2.27, 1.94(2s, 3H); 2.19(m, 2H); 1.82(m, 3H); 1.46(m, 8H); 0.95(d, 6H). |
| 12. | 7.89, 7.86(2d, 2H); 7.66, 7.46(2t, 2H); 6.78(s, 1H); 6.10, 7.66(2m, 2H); 5.66, 5.54(2s, 1H); 5.54(s, 1H); 4.87(s, 2H); 4.48(t, 2H); 3.90(d, 2H); 2.65 (s, 3H); 2.31, 1.97(2s, 3H); 2.19(m, 2H); 1.86(m, 2H); 1.79(s, 3H); 1.45(m, 8H). |
| 13. | 7.88, 7.87(2d, 2H); 7.63, 7.41(2t, 2H); 7.21(m, 1H); 6.13(m, 2H); 5.74(d, 1H); 5.23(1H); 4.48(t, 2H); 4.01(m, 1H); 2.21(2H, m); 1.86, 1.75, 1.47(3m, 11H); 1.12(d, 3H); 0.92(d, 6H). |
| 14. | 8.03, 7.87(2d, 2H); 7.70, 7.49(2t, 2H); 7.04(s, 1H); 6.06, 7.49(2m, 2H); 5.60, 5.40(2s, 1H); 5.41(1H); 4.46(t, 2H); 3.14(t, 2H); 2.28, 1.93(2s, 3H); 2.19(m, 2H); 1.86(m, 3H); 1.47(m, 8H); 0.93(d, 6H). |
| 15. | 8.12, 7.86(2d, 2H); 7.68, 7.47(2t, 2H); 7.21(m, 1H); 7.04(s, 1H); 6.10(m, 2H); 5.76(d, 1H); 5.54(t, 1H); 4.46(t, 2H); 3.18(t, 2H); 2.17(m, 2H); 1.82(m, 3H); 1.44(m, 8H); 0.91(d, 6H). |
| 16. | 8.04, 7.93(2d, 2H); 7.70, 7.48(2t, 2H); 7.22(s, 1H); 6.05(m, 2H); 5.57(s, 1H); 5.48(s, 1H); 4.49(t, 2H); 3.23(t, 2H); 2.25(s, 3H); 2.15(m, 2H); 1.80(m, 2H); 1.40(m, 8H). |
| 17. | 7.90(d, 1H); 7.89(s, 1H); 7.70(d, 2H); 6.91(d, 1H); 6.05, 7.58(2m, 2H); 5.59, 5.51(2s, 1H); 5.57(t, 1H); 4.44(t, 2H); 3.12(t, 2H); 2.28, 1.95(2s, 3H); 2.17(m, 2H); 1.82(m, 3H); 1.43(m, 8H); 0.92(d, 6H). |
| 18. | 7.90(d, 1H); 7.70(d, 2H); 7.28(s, 1H); 7.20(m, 1H); 6.91(d, 1H); 6.03(m, 2H); 5.75(d, 1H); 5.46(t, 1H); 4.45(t, 2H); 3.17(t, 2H); 2.19(m, 2H); 1.84(m, 3H); 1.45(m, 8H); 0.94(d, 6H). |
| 19. | 8.18(s, 1H); 7.85(m, 2H); 7.55(d, 1H); 6.86(d, 1H); 6.04(2m, 2H); 5.58, 5.50(2s, 1H); 4.93(s, 1H); 4.46(t, 2H); 3.14(t, 2H); 2.26, 1.94(2s, 3H); 2.18(m, 2H); 1.83, 1.40(2m, 11H); 0.91(d, 6H). |
| 20. | 7.93(d, 1H); 7.82(m, 1H); 7.37(m, 2H); 6.94(d, 1H); |

TABLE II-continued

Characterising data for compounds of formula (I)
Nuclear Magnetic Resonance Data

| Compound No. | Details of Spectrum |
|---|---|
|  | 6.08(2m, 2H); 5.60, 5.51(2s, 1H); 5.45(1H); 4.46(t, 2H); 3.15(t, 2H); 2.30, 1.93(2s, 3H); 2.15(m, 2H); 1.81, 1.45(2m, 11H); 0.91(d, 6H). |
| 21. | 8.26(s, 1H); 7.83(d, 1H); 7.67, 7.40(2m, 3H); 6.06(2m, 2H); 5.60, 5.52(2s, 1H); 5.47(s, 1H); 4.53(t, 2H); 3.15(t, 2H); 2.27, 1.95(2s, 3H); 2.18(m, 2H); 1.77(m, 3H); 1.45(m, 8H); 0.95(d, 6H). |
| 22 | 7.87(d, 1H); 7.63(m, 3H); 7.42(t, 1H); 6.05, 7.61(2m, 2H); 5.60, 5.52(2s, 1H); 5.44(1H); 4.57(t, 2H); 3.25(t, 2H); 2.28, 1.94(2s, 3H); 2.20, 1.87, 1.45(3m, 13H); 0.95(d, 6H). |
| 23 | 7.96, 7.51, 6.94(3d, 3H); 7.27(m, 2H); 6.05, 7.55(2m, 2H); 5.60, 5.53(2s, 1H); 5.46, (1H); 4.56(t, 2H); 3.20(t, 2H); 2.29, 1.95(2s, 3H); 2.18, 1.84, 1.43(3m, 13H); 0.96(d, 6H). |
| 24 | 7.90, 7.77, 7.55, 6.92(4d, 4H); 7.69(s, 1H); 7.17(m, 1H); 6.12(m, 2H); 5.76(d, 1H); 5.50(1H); 4.47(t, 2H); 3.20(t, 2H); 2.19, 1.84, 1.48(3m, 13H); 0.92(d, 6H). |
| 25 | 7.88, 7.77, 7.58, 6.95(4d, 4H); 7.70(s, 1H); 6.05, 7.58(2m, 2H); 5.60, 5.52(2s, 1H); 5.50(1H); 4.46(t, 2H); 3.17(t, 2H); 2.28, 1.94(2s, 3H); 2.19, 1.84, 1.48(3m, 13H); 0.93(d, 6H). |
| 26 | 8.06, 7.97, 7.80, 6.97(4d, 4H); 8.04(s, 1H); 7.20(m, 1H); 6.10(m, 2H); 5.77(d, 1H); 5.48(1H); 4.48(t, 2H); 3.15(t, 2H); 2.20, 1.86, 1.43(3m, 13H); 0.91(d, 6H). |
| 27 | 8.02, 7.92, 7.78, 6.99(4d, 4H); 8.00(s, 1H); 6.04, 7.58(2m, 2H); 5.60, 5.52(2s, 1H); 5.48(1H); 4.49(t, 2H); 3.13(t, 2H); 2.27, 1.93(2s, 3H); 2.18, 1.83, 1.48(3m, 13H); 0.92(d, 6H). |
| 28 | 8.11(s, 1H); 7.85(d, 1H); 7.68(t, 1H); 7.43(t, 1H); 6.07, 7.57(2m, 2H); 5.62, 5.54(2s, 1H); 5.49(1H); 4.56(t, 2H); 3.19(t, 2H); 2.29, 1.96(2s, 3H); 2.21, 1.88, 1.45(3m, 13H); 0.94(d, 6H). |
| 29 | 8.10, 7.79(2d, 2H); 7.60, 7.35(t, 2H); 6.24(s, 1H); 6.04, 7.58(2m, 2H); 5.58, 5.50(2s, 1H); 5.49(1H); 4.45(t, 2H); 4.02(s, 3H); 3.11(t, 2H); 2.27, 1.94(2s, 3H); 2.19, 1.82, 1.46(3m, 13H); 0.92(d, 6H). |
| 30 | 8.42(s, 1H); 7.78(m, 3H); 7.48(m, 1H), 7.57, 6.06(2m, 2H); 5.62, 5.52(2s, 1H); 5.49(1H); 4.56(t, 2H); 3.16(t, 2H); 2.27, 1.95(2s, 3H); 2.17, 1.85, 1.44(3m, 13H); 0.95(d, 6H). |
| 31 | 8.67(s, 1H); 7.74(m, 3H); 7.50(t, 1H); 7.58, 6.06(2m, 2H); 5.61, 5.52(2s, 1H); 5.48(1H); 4.60(t, 2H); 3.15(t, 2H); 2.28, 1.94(2s, 3H); 2.17, 1.86, 1.45(3m, 13H); 0.94(d, 6H). |
| 32 | 7.97, 7.74, 7.64, 6.97(4d, 4H); 7.27(m, 1H); 6.06, 7.56(2m, 2H); 5.60, 5.51(2s, 1H); 5.47(1H); 4.55(t, 2H); 3.13(t, 2H); 2.27, 1.94(2s, 3H); 2.18, 1.86, 1.44(3m, 13H); 0.93(d, 6H). |
| 33 | 7.98(d, 1H); 7.86(d, 1H); 7.73(d, 1H); 7.63(t, 1H); 7.39(t, 1H); 6.90(d, 1H); 6.56(d, 1H); 6.38(1H); 6.10, 6.04 (2t, 1H); 4.47(t, 2H); 3.18(t, 2H); 2.30(d, 3H); 2.25(m, 2H) 1.87, 1.41(m, 11H); 0.93(d, 6H). |
| 34 | 7.98(d, 1H); 7.85(d, 1H); 7.72(d, 1H); 7.66(t, 1H); 7.40(t, 1H); 6.88(d, 1H); 6.43 (1H); 6.10, 6.06(2t, 1H); 4.87(s, 2H); 4.48(t, 2H); 3.90(d, 2H); 3.48(m, 1H); 2.31(d, 3H); 2.22(m, 2H); 1.80(m, 2H); 1.70(m, 2H); 1.44(m, 8H). |
| 35 | 7.97(d, 1H); 7.86(d, 1H); 7.72(d, 1H); 7.60(t, 1H); 7.36(t, 1H); 6.88(d, 1H); 6.57(d, 1H); 6.31(1H); 6.08, 6.01(2t, 1H); 4.50(t, 2H); 3.15(t, 2H); 2.26(d, 3H); 2.22(m, 2H); 1.83, 1.48(m's, 11H); 0.95(s, 9H). |
| 36 | 8.01(d, 1H); 7.82(d, 1H); 7.72(d, 1H); 7.62(t, 2H); 7.39(t, 2H); 7.00(2d, 1H); 6.88(d, 1H); 6.02(d, 1H); 5.58(1H); 5.13(2t, 1H); 4.46(t, 2H); 3.20(t, 2H); 2.24(m, 2H); 1.85, 1.42(m's, 11H); 0.93(d, 6H) |
| 37 | 7.98(d, 1H); 7.84(d, 1H); 7.72(d, 1H); 7.63(t, 1H); 7.37(t, 1H); 7.00(2d, 1H); 6.91(d, 2H); 6.03(d, 1H); 5.35(1H); 5.15(2t, 1H); 4.45(t, 2H); 3.96(m, 1H); 2.23(m, 2H); 1.87(m, 2H); 1.76(m, 1H); 1.38(m, 8H); 1.13(d, 3H); 0.91(d, 3H) |
| 38 | 7.99(d, 1H); 7.84(d, 1H); 7.73(d, 1H); 7.63(t, 1H); 7.39(t, 1H); 6.90(d, 1H); 6.60(1H); 6.05(s, 1H); 5.24(2t, 1H); 4.47(t, 2H); 3.18(t, 2H); 2.25(s, 3H); 2.22(m, 2H); 1.84, 1.40(m's, 11H); 0.95(d, 6H) |
| 39 | 7.97(d, 1H); 7.83(d, 1H); 7.72(d, 1H); 7.60(t, 1H); 7.35(t, 1H); 6.90(d, 1H); 6.48, 6.33(2d, 1H); 6.30(1H); 5.29, 5.18(2t, 1H); 4.49(t, 2H); 3.20(t, 3H); 2.24(m, 2H); 1.87, 1.40(m's, 11H); 0.95(d, 6H) |
| 40 | 7.97(d, 1H); 7.84(d, 1H); 7.72(d, 1H); 7.61(t, 1H); 7.35(t, 1H); 6.91(d, 1H); 6.42(1H); 5.35, 5.20(2t, 1H); 4.46(t, 2H); 3.20(t, 2H); 2.23(d, 3H); 2.21(m, 2H); 1.85, 1.40(m's, 11H); 0.93(d, 6H) |
| 41 | 7.97(d, 1H); 7.83(d, 1H); 7.70(d, 1H); 7.61(t, 1H); 7.35(t, 1H); 6.88(d, 1H); 6.55(d, 1H); 6.10(1H); 6.07, 5.99(2t, 1H); 4.45(t, 2H); 3.92(m, 1H); 2.28(d, 3H); 2.22(m, 2H); 1.80, 1.42(m's, 11H); 1.13(d, 3H); 0.93(d, 6H) |
| 42 | 7.97(d, 1H); 7.81(d, 1H); 7.70(d, 1H); 7.59(t, 1H); 7.37(t, 1H); 6.88(d, 1H); 6.56(d, 1H); 6.09, 601 (2t, 1H); 6.07(1H); 4.46(t, 2H); 3.95(m, 1H); 2.27 (d, 3H); 2.20(m, 2H); 1.83(m, 2H); 1.45(m, 12H); 1.16(d, 3H); 0.90(t, 3H) |
| 43 | 7.86(m, 2H); 7.62(t, 1H); 7.41(t, 1H); 6.76(s, 1H); 6.57(d, 1H); 6.33(1H); 6.10, 6.04(2t, 1H); 4.47(t, 2H); 3.18(t, 2H); 2.64(s, 3H); 2.29(d, 3H); 2.22(m, 2H); 1.81, 1.48(m's, 11H); 0.96(d, 6H) |
| 44 | 7.91(d, 1H); 7.89(s, 1H); 7.70(d, 1H); 6.90(d, 1H); 6.55(d, 1H); 6.33(1H); 6.07, 6.00(2t, 1H); 4.41(t, 2H); 3.15(t, 2H); 2.27(d, 3H); 2.20(m, 2H); 1.81, 1.41(m's, 11H); 0.94(d, 6H) |
| 45 | 7.97(d, 1H); 7.85(d, 1H); 7.71(d, 1H); 7.62(t, 1H); 7.38(t, 1H); 6.98(d, 1H); 6.66, 6.52(2d, 1H); 6.35; 6.26(2d, 1H); 6.09, 6.03(2t, 1H); 4.48(t, 2H); 3.18(t, 2H); 2.18(2H, m); 1.85, 1.43(m's, 11H); 0.93(d, 6H). |
| 46 | 7.97(d, 1H); 7.86(d, 1H); 7.70(d, 1H); 7.62(t, 1H); 7.37(t, 1H); 6.88(d, 1H); 6.65, 6.50(2d, 1H); |
| 47 | 7.96(d, 1H); 7.84(d, 1H); 7.72(d, 1H); 7.63( , 1H); 7.38(t, 1H); 6.99(d, 1H); 6.20(1H); 6.18, 6.02(2t, 1H); 4.50(t, 2H) 3.19(t, 2H); 2.23(m, 2H); 1.84, 1.40(m's, 15H); 0.92(6H. d) |
| 48 | 7.97(d, 1H); 7.85(d, 1H); 7.72(d, 1H); 7.63(t, 1H); 7.39(t, 1H); 6.88(d, 1H); 6.26(1H); 6.18, 6.03(2t, 1H); 4.88(s, 2H); 4.47(t, 2H) .89(d, 2H); 1.86, 1.40(m's, 15H); 1.58(d, 3H). |
| 49 | 7.97(d, 1H); 7.84(d, 1H); 7.73(d, 1H); 7.62(t, 1H); 7.40(t, 1H); 6.91(d, 1H); 6.27(1H); 4.47(t, 2H); 3.17(t, 2H); 2.19(d) 1.63(s, 3H); 2.17(2H, m); 1.80, 1.38(m's, 15H); 0.94(d, 6H). |
| A1 | 8.19, 8.03, 7.18(3d, 3H); 7.70(t, 1H); 7.59(d, 1H); 7.48(t, 1H); 6.02, 7.48(2m, 2H); 5.56, 5.49(2s, 1H); 5.51(1H); 4.80(s, 2H) 3.58(t, 2H); 3.15(t, 2H); 2.24, 1.90(2s, 3H); 2.16(m, 2H); 1.78, 1.67, 1.42(3m, 11H); 0.91(d, 6H). |
| A2 | 7.96, 7.83, 7.74(3d, 3H); 7.60, 7.37(2t, 2H); 6.05, 7.56(2m, 2H); 5.59, 5.50(2s, 1H); 5.49(1H); 4.47(t, 2H); 3.12(t, 2H); 2.25, 1.92(2s, 3H); 2.18, 1.84, 1.47(m, 11H); 0.92(d, 6H). |
| A3 | 7.79(2d, 2H); 7.38-7.75(m, 3H); 7.22(m, 1H); 6.04, (2m, 2H); 5.59, 5.51(2s, 1H); 5.51(1H); 3.35(t, 2H); 3.13(t, 2H); 2.26, 1.93(2s, 3H); 2.18(m, 2H); 1.78(m, 3H); 1.22-1.60(m, 6H); 0.93(d, 6H). |
| A4 | 8.00, 7.84, 7.71(3d, 3H); 7.62(t, 1H); 7.48(m, 1H); 7.40(t, 1H); 7.27(t, 1H); 6.92(d, 1H); 6.20(d, 1H); 6.16(m, 2H); 4.45(t, 2H); 3.58(t, 2H); 2.14(m, 2H); 2.01(m, 1H); 1.81(m, 2H); 1.53(m, 8H); 0.97(d, 6H). |
| A5 | 8.00, 7.84, 7.73, 6.90(4d, 4H); 7.66, 7.41(2t, 2H); 7.24(m, 1H); 6.17(m, 1H); 5.75(d, 1H); 5.48(1H); 4.48(t, 2H); 3.20(t, 2H); 2.30, 1.86, 1.70(3m, 7H); 0.96(d, 6H). |
| A6 | 8.01, 7.85, 7.74, 6.90(4d, 4H); 7.65, 7.40(2t, 2H); 7.22(m, 1H); 6.17(m, 2H); 5.76(d, 1H); 5.37(1H); 4.50(t, 2H); 3.98(m, 1H); 2.28, 1.88, 1.69(3m, 7H); 1.12(d, 3H); 0.94(m, 6H). |
| A7 | 8.01, 7.83, 7.72, 6.90(4d, 4H); 7.65, 7.40(2t, 2H); 7.62, 6.10 (2m, 2H); 5.60, 5.52(2s, 1H); 5.47(1H); 4.50(t, 2H) 3.16(t, 2H); 2.30, 1.97(2s, 3H); 2.29, 1.87, 1.65(3m, 7H); 0.94(d, 6H). |
| A8 | 8.00, 7.84, 7.73, 6.90(4d, 4H); 7.64, 7.39(2t, 2H); |

TABLE II-continued

Characterising data for compounds of formula (I)
Nuclear Magnetic Resonance Data

| Compound No. | Details of Spectrum |
|---|---|
|  | 7.62, 6.08(2m, 2H); 5.60, 5.52(2s, 1H); 5.55(1H); 4.85(s, 2H); 4.48(t, 2H); 3.86(d, 2H); 2.27, 1.95(2s, 3H); 1.75(s, 3H). |
| A9 | 7.98, 7.83, 7.71, 6.88(4d, 4H); 7.60, 7.38(2t, 2H); 7.20(m, 1H) 6.12(m, 2H); 5.74(d, 1H); 5.44(1H); 4.47(t, 2H); 3.18(t, 2H) 2.21, 1.84, 1.55(3m, 9H); 2.29, 1.88, 1.65(3m, 7H); 0.94(d, 6H). |
| A10 | 7.98, 7.84, 7.72, 6.90(4d, 4H); 7.61, 7.38(2t, 2H); 7.58, 6.07(2m, 2H); 5.59, 5.51(2s, 1H); 5.47(1H); 4.46(t, 2H); 3.14(t, 2H); 2.28, 1.94(2s, 3H); 2.20, 1.85, 1.53(3m, 9H); 0.93(d, 6H); |
| A11 | 7.98, 7.84, 7.73, 6.91(4d, 4H); 7.62, 7.38(2t, 2H); 7.60, 6.08(2m, 2H); 5.61, 5.53(2s, 1H); 5.50(1H); 4.87(s, 2H); 4.48(t, 2H); 3.87(d, 2H); 2.31, 1.96(2s, 3H); 1.78(s, 3H); 2.24, 1.86, 1.57(3m, 9H). |
| A12 | 7.97, 7, 83, 7.72, 6.90(4d, 4H); 7.61, 7.38(2t, 2H); 5.56 (s, 1H); 5.42(1H); 4.48(t, 2H); 3.16(t, 2H); 2.17, 1.84 (2s, 3H); 2.09(t, 2H); 1.83, 1.48, 1.32(3m, 15H); 0.95 (d, 6H). |
| A13 | 8.09, 8.05, 7.80, 7.33(4d, 4H); 7.72, 7.51(2t, 2H); 7.57, 6.05(2m, 2H); 5.61, 5.51(2s, 1H); 5.55(1H); 3.14 (t, 2H); 2.98(t, 2H) 2.28, 1.95(2s, 3H); 2.16, 1.80, 1.38, 1.30(4m, 15H); 0.92(d, 6H). |
| A14 | 9.12, 8.68, 7.66(3d, 3H); 8.05(m, 2H); 7.81(t, 1H); 6.05, 7.53(2m, 2H); 5.70, 5.55(2s, 1H); 7.64(1H); 3.56(t, 2H); 3.17(d, 2H); 2.27, 1.95(2s, 3H); 2.15, 1.88, 1.32(3m, 15H); 0.93(d, 6H). |
| A15 | 7.98, 7.83, 7.73, 6.97(4d, 4H); 7.65, 7.39(2t, 2H); 6.03, 7.5(2m, 2H); 5.58, 5.50(2s, 1H); 5.44(1H); 4.67 (m, 2H); 3.85(m, 2H); 3.57(m, 2H); 3.13(t, 2H); 2.26, 1.94(2s, 3H); 2.17, 1.86, 1.60, 1.53(4m, 7H); 0.93 (d, 6H). |
| B1 | 8.72, 8.15(2d, 2H); 8.04(s, 1H); 7.46(m, 1H); 6.74 (m, 1H); 6.03, 7.59(2m, 2H); 5.58, 5.55(2s, 1H); 5.62(1H); 4.20(t, 2H); 3.14(t, 2H); 2.24, 1.94 (2s, 3H); 2.18, 1.91, 1.81, 1.3–1.6(4m, 11H). |
| B2 | 8.28, 8.18(2d, 2H); 7.83, 7.55(2t, 2H); 7.06(s, 1H); 6.06, 7.54(2m, 2H); 5.58, 5.51(2s, 1H); 5.48(1H); 4.38(t, 2H); 3.16(t, 2H); 2.27, 1.92(2s, 3H); 2.20, 1.99, 1.81, 1.56(4m, 11H); 0.92(d, 6H). |
| B3 | 8.55(d, 1H); 7.60(m, 1H); 7.35(m, 1H); 6.85(d, 1H); 6.03(2m, 2H); 5.55(2s, 1H); 4.12(t, 2H); 3.12(t, 2H); 2.25, 1.90(2s, 3H); 2.18, 1.80, 130–1.65(3m, 11H); 0.90(d, 6H). |
| B4 | 8.50(d, 1H); 7.60(m, 1H); 7.35(m, 1H); 6.85(d, 1H); 6.05(2m, 2H); 5.62(2s, 1H); 4.12(t, 2H); 3.10(t, 2H); 2.25, 1.90(2s, 3H); 2.30, 1.62–2.05(2m, 7H); 0.90 (d, 6H). |
| B5 | 8.18(m, 2H); 7.69(m, 1H); 7.48(m, 1H); 7.12(d, 1H); 6.06(2m, 2H); 5.62, 5.51(2s, 1H); 5.47( , 1H); 4.11 (t, 2H); 3.13(t, 2H); 2.28, 1.92(2s, 3H); 2.15, 1.88, 1.50(3m, 13H); 0.93(d, 6H). |
| B6 | 8.18(m, 2H); 7.69(d, 1H); 7.48(m, 1H); 7.12(d, 1H); 6.06(2m, 2H); 5.61, 5.50(2s, 1H); 5.50(1H); 4.84 (s, 2H); 4.11(t, 2H); 3.88(d, 2H); 2.30, 1.95(2s, 3H); 2.18(m, 2H); 1.88(m, 2H); 1.77(m, 3H); 1.26–1.80 (m, 8H). |
| B7 | 8.86(m, 1H); 8.12(d, 1H); 7.43(m, 3H); 7.17(m, 1H); 7.05(d, 1H); 6.12(m, 2H); 5.72(d, 1H); 5.26(1H); 4.27 (t, 2H); 3.97(m, 1H); 2.27(m, 2H); 2.06(m, 2H); 1.71 (m, 3H); 1.11(d, 3H); 0.92(d, 6H). |
| B8 | 8.82(d, 1H); 8.30(m, 1H); 7.66(d, 1H); 7.20(m, 1H); 6.60(d, 1H); 6.12(m, 2H); 5.72(d, 1H); 5.23(1H); 4.23 (t, 2H); 3.98(m, 1H); 2.28(m, 2H); 1.99(m, 2H); 1.76(m, 3H); 1.12(d, 3H); 0.93(d, 6H). |
| B9 | 8.92(m, 1H); 8.46(d, 1H); 8.01(s, 1H); 7.53(m, 1H); 7.18(m, 1H); 6.14(m, 2H); 5.74(d, 1H); 5.24(1H); 4.38 (t, 2H); 3.97(m, 1H); 2.29(m, 2H); 1.98(m, 2H); 1.77 (m, 3H); 1.12(d, 3H); 0.91(d, 6H). |
| B10 | 8.05, 7.87(2d, 2H); 7.58(t, 1H); 7.33(t, 1H); 6.22 (s, 1H); 6.03, 7.58(2m, 2H); 5.59, 5.50(2s, 1H); 5.5(1H); 4.45(t, 2H); 4.02(s, 3H); 3.14(t, 2H); 2.28, 1.94(2s, 3H); 2.20, 1.82, 1.50(3m, 11H); 0.92(d, 6H). |
| C1 | 8.46, 7.09, 6.50(3d, 3H); 7.64(m, 1H); 7.51(m, 2H); 6.02, 7.62(2m, 2H); 5.59, 5.51(2s, 1H); 5.50(1H); 4.03(t, 2H); 3.15(t, 2H); 2.26, 1.93(2s, 3H); 2.18, 1.82, 1.40(3m, 11H); 0.93(d, 6H). |
| C2 | 8.23, 7.26(2d, 2H); 7.67(m, 1H); 7.53(m, 1H); 6.05, 7.57(2m, 2H); 5.59, 5.51(2s, 1H); 5.47(1H); 4.54 (t, 2H); 3.17(t, 2H); 2.27, 1.95(2s, 3H); 2.20(m, 2H); 1.90, 1.81, 1.50(3m, 9H); 0.96(d, 6H). |
| C3 | 8.96(s, 1H); 7.88(d, 1H); 7.71(d, 1H); 7.59(m, 1H); 7.38(m, 1H); 7.02(s, 1H); 6.07, 7.58(2m, 2H); 5.61, 5.53(2s, 1H); 4.35(t, 2H); 3.15(t, 2H); 2.27, 1.96 (2s, 3H); 2.18(m, 2H); 1.85(m, 3H); 1.44(m, 10H); 0.95(d, 6H). |
| C4 | 9.34(s, 1H); 7.62(d, 1H); 7.45(m, 2H); 7.01(s, 1H); 6.05, 7.52(2m, 2H); 5.62, 5.53(2s, 1H); 5.52(1H); 4.38(t, 2H); 3.16(t, 2H); 2.26, 1.95(2s, 3H); 2.20 (m, 2H); 1.87(m, 3H); 1.44(m, 10H); 0.93(d, 6H). |
| C5 | 8.03, 7.69(2d, 2H); 7.56, 7.37(2t, 2H); 6.82(s, 1H); 6.05, 7.54(2m, 2H); 5.60, 5.51(2s, 1H); 5.48(1H); 4.23 (t, 2H); 3.18(t, 2H); 2.94(s, 3H); 2.28, 1.95(2s, 3H); 2.20, 1.84, 1.45(3m, 13H); 0.96(d, 6H). |
| C6 | 8.92, 7.19, 6.90(3s, 3H); 7.83, 7.30(2d, 2H); 6.06, 7.56 (2m, 2H); 5.57, 5.49(2s, 1H); 5.47(1H); 4.31(t, 2H); 3.14(t, 2H); 2.28, 1.95(2s, 3H); 2.18, 1.83, 1.43 (3m, 13H); 0.95(d, 6H). |
| C7 | 8.21, 7.70(2d, 2H); 7.64, 7.47(2t, 2H); 6.94(s, 1H); 6.05, 7.55(2m, 2H); 5.61, 5.51(2s, 1H); 5.48(1H); 4.32 (t, 2H); 3.16(t, 2H); 2.27, 1.93(2s, 3H); 2.18, 1.83, 1.41(3m, 13H); 0.94(d, 6H). |
| D1 | 7.92, 7.83(2d, 2H); 7.68, 7.56(2t, 2H); 6.04, 7.61 (2m, 2H); 5.57, 5.49(2s, 1H); 5.61(1H); 4.52(t, 2H); 3.12(t, 2H); 2.24, 1.92(2s, 3H); 2.17(m, 2H); 1.90, 1.80, 1.45(3m, 11H); 0.91(d, 6H). |
| D2 | 8.34(m, 2H); 7.96(m, 1H); 6.05, 7.61(2m, 2H); 5.61, 5.50(2s, 1H); 5.61(1H); 4.65(t, 2H); 3.14(t, 2H); 2.26, 1.95(2s, 3H); 2.20(m, 2H); 1.96, 1.83, 1.51 (3m, 11H); 0.95(d, 6H). |
| D3 | 8.17(d, 1H); 7.87(m, 2H); 7.67(m, 1H); 6.06, 7.60 (2m, 2H); 5.60, 5.52(2s, 1H); 5.49(1H); 4.60(t, 2H); 3.14(t, 2H); 2.26, 1.95(2s, 3H); 2.21(m, 2H); 1.91, 1.80, 1.49(3m, 11H); 0.92(d, 6H). |
| D4 | 7.58, 7.25(2m, 4H); 7.27(s, 1H); 6.03, 7.60(2m, 2H); 5.61, 5.52(2s, 1H); 5.60(1H); 4.48(t, 2H); 3.14(t, 2H); 2.27, 1.96(2s, 3H); 2.17(m, 2H); 1.81, 1.75, 1.35 (3m, 12H); 0.94(d, 6H). |
| D5 | 7.67(m, 2H); 7.36, 7.23(2t, 2H); 6.04, 7.56(2m, 2H); 5.60, 5.51(2s, 1H); 5.48(1H); 4.55(t, 2H); 3.14(t, 2H); 2.27, 1.95(2s, 3H); 2.16, 1.84, 1.35(3m, 13H); 0.95 (d, 6H). |
| D6 | 7.77(m, 2H); 7.29(m, 2H); 6.57(d, 1H); 6.37(1H); 6.09, 6.03(2t, 1H); 4.56(t, 2H); 3.18(t, 2H); 2.28(d, 3H); 2.22(m, 2H); 1.83, 1.40(m's, 11H); 0.92(d, 6H). |

TABLE III

Characterising data for compounds of formula (I) - Physiochemical data

| Compound No. | 2E/4E:2Z/4E % | Chromatography Rf | Solvent | m.p/°C. |
|---|---|---|---|---|
| 1 | 55:45 | 0.23 | A |  |
| 2 | NA |  |  | 80–2° |
| 3 | >95% 2E, 4E | 0.23 | A |  |
| 4 | NA | 0.28 | A |  |
| 5 | NA | 0.66 | B |  |
| 6 | NA | 0.21 | B |  |
| 7 | NA | 0.50 | B | 89° |
| 8 | 70:30 | 0.71 | B |  |
| 9 | 60:40 | 0.65 | B |  |
| 10 | NA | 0.45 | B | 88–9° |
| 11 | 55:45 | 0.22 | A |  |
| 12 | 50:50 | 0.26 | A | 113° |
| 13 | NA | 0.14 | A | 92° |
| 14 | 65:35 | 0.24 | A |  |
| 15 | NA | 0.48 | B | 78° |
| 16 | >95% 2E, 4E |  |  | 89° |
| 17 | 50:50 | 0.63 | B | 79–80° |
| 18 | NA | 0.45 | B | 127° |
| 19 | 55:45 |  |  | 80–3° |
| 20 | 55:45 | 0.65 | B |  |

TABLE III-continued

Characterising data for compounds of formula (I) - Physiochemical data

| Compound No. | 2E/4E:2Z/4E % | Chromatography Rf | Solvent | m.p/°C. |
|---|---|---|---|---|
| 21 | 65:35 | 0.56 | B | |
| 22 | 50:50 | 0.57 | B | |
| 23 | 50:50 | 0.56 | B | |
| 24 | NA | 0.46 | B | 129-30° |
| 25 | 50:50 | 0.23 | A | |
| 26 | NA | 0.54 | B | 122° |
| 27 | 60:40 | 0.28 | A | 84-5° |
| 28 | 50:50 | 0.61 | B | |
| 29 | 80:20 | 0.17 | A | |
| 30 | 90:10 | 0.56 | B | 82-4° |
| 31 | 65:35 | 0.50 | B | 78-82° |
| 32 | 60:40 | 0.52 | B | |
| 33 | | 0.46 | A | 59° |
| 34 | | 0.44 | A | |
| 35 | | 0.50 | A | |
| 36 | | 0.44 | A | |
| 37 | | 0.42 | A | |
| 38 | | 0.30 | | |
| 39 | | 0.48 | A | 73° |
| 40 | | 0.17 | | 75-6° |
| 41 | | 0.47 | A | 81° |
| 42 | | 0.59 | B | 65-6° |
| 43 | | 0.59 | B | 57-9° |
| 44 | | 0.77 | B | |
| 45 | | 0.54 | B | 112-4° |
| 46 | | 0.50 | B | 114-5° |
| 47 | | 0.40 | A | |
| 48 | | 0.62 | B | 91-3° |
| 49 | | 0.54 | | 49-50° |
| A1 | 50:50 | 0.39 | B | |
| A2 | 60:40 | 0.55 | B | |
| A3 | 65:35 | 0.52 | B | |
| A4 | NA | 0.77 | B | |
| A5 | NA | 0.50 | B | 106-7° |
| A6 | NA | 0.52 | B | 105-7° |
| A7 | 65:35 | 0.66 | B | 74-80° |
| A8 | 50:50 | 0.66 | B | |
| A9 | NA | 0.69 | B | 101° |
| A10 | 65:35 | 0.71 | B | |
| A11 | 60:40 | 0.73 | B | |
| A12 | 75:25 | 0.71 | B | |
| A13 | 60:40 | 0.44 | B | |
| A14 | 60:40 | | | |
| A15 | 65:35 | 0.59 | B | |
| B1 | 60:40 | | | |
| B2 | 80:20 | 0.67 | B | |
| B3 | 50:50 | 0.40 | C | |
| B4 | 85:15 | 0.20 | C | |
| B5 | 85:15 | 0.20 | D | 101.3° |
| B6 | 50:50 | 0.20 | D | |
| B7 | NA | 0.11 | B | |
| B8 | NA | 0.42 | E | |
| B9 | NA | | | 145-6° |
| B10 | 50:50 | 0.54 | B | |
| C1 | 65:35 | | | |
| C2 | 60:40 | | | |
| C3 | 50:50 | 0.52 | B | |
| C4 | 55:45 | 0.54 | B | |
| C5 | 50:50 | 0.57 | B | |
| C6 | 50:50 | 0.65 | B | 92-5° |
| C7 | 55:45 | 0.59 | B | |
| D1 | 60:40 | | | |
| D2 | 65:35 | 0.44 | B | |
| D3 | 35:65 | 0.52 | B | |
| D4 | 60:40 | 0.09 | B | |
| D5 | 55:45 | 0.71 | B | |
| D6 | | 0.39 | A | |

2E/4E:2Z/4E ratios to the nearest 5%
A: Ether/hexane (1/1)
B: Ether
C: Hexane/ethyl acetate (3/2)
D: Hexane/ethyl acetate (5/1)
E: Ether/ethyl acetate (7/3)

BIOLOGICAL EXAMPLES

Spray Tests

Test solutions were made up by dissolving the compound in acetone and adding to water/wetter to give an acetone emulsion.

*Musca domestica*

20 female Musca were contained in a cardboard cylinder with gauze over either end. Solution containing the compound was sprayed onto the insects so enclosed and mortality assessed after 48 hours at 25° C.

The following compounds were active at 1000 ppm:
4,9,20,21,22,28,34,41
A4,A9,A10,A11,B2,C4,C5,C7

The following compounds were active at 200 ppm:
1,2,3,5,6,7,8,10,11,12,13,14,15,16,23,29,D5,33,38,40,4-5,46,47

*Sitophilus granarius* and *Tribolium castaneum*

20 adult Sitophilus and Tribolium were added to 10 g wheat which had been previously treated with 2 ml of the solution containing the compound. Mortality was assessed after 6 days at 25° C.

*S. Granarius*

The following compounds were active at 1000 ppm:
3,5,6,11,12,13,14,16,A5,A6,D2,33,34

*T. Castaneum*

The following compounds were active at 1000 ppm:
1,2,12,C1,33,34

*Plutella xylostella*

7 Plutella larvae were put onto chinese cabbage leaf discs and sprayed with the solution containing the compound. Mortality was assessed after 2 days at 25° C.

The following compounds were active at 200 ppm:
4,6,7,8,9,13,15,16,17,18,19,20,21,25,26,27,28,29,30,31-,44,45,48
A1,A2,A3,A4,A5,A7,A8,A9,A10,A11,A12
B2,B3,B4,B5,B6,B7,B10,C1,C2,C3,C6,C7,D2,D3,D-4,D5.

The following compounds were active at up to 40 ppm: 33,38,40,41,45,46,47.

*Diabrotica undecimpunctata*

2nd instar larvae and their food were sprayed on filter paper with the solution containing the compound. Activity was assessed at 2 days.

The following compounds were active at 1000 ppm:
25,28,29,A9,B10,40,41,42,47,48

*Spodoptera littoralis*

Uninfested leaves were sprayed with the test solution containing the compound and allowed to dry. These were then infested with 10 newly hatched larvae. Mortality was assessed after 3 days.

The following compounds were active at 1000 ppm:
7,9,10,11,13,14,15,16,17,18,20,21,22,23,25,27,28,29,30-,31,40,44,45
A2,A4,A9,A10,A11-,A12,B2,B6,B10,C3,C4,C5,C7,D2

The following compound were active at 200 ppm:
D5,33,34,41,47,38

*Myzus persicae*

10 adult Myzus were placed on a leaf disc of chinese cabbage. 24 hours later the disc was sprayed with a solution containing the compound. Mortality was assessed after 2 days at 25° C.

The following compounds were active at 1000 ppm:
11,16,21,26,27,A1,A2,A3-,A10,B4,B6,B7,B9,C3,C6,D2

*Tetranychus urticae*

Leaf discs of infested french bean were sprayed with the solution containing the compound. Mortality was assessed after 2 days at 25° C.

The following compounds were active at 1000 ppm:

4,7,9,15,17,19,20,30,31,A2,A4,A8,A10,A11,B2,B3,C3,C7,D1,43,44,45,47,48

The following compounds were active at 200 ppm:
1,2,3,5,8,10,11,13,14,21,22,23,28,29,A12,D5,33,34,40,41,46

Topical Application Tests

*Musca domestica*

The activity of compounds of the invention against unanaesthetised female *Musca domestica* (WRL strain), was demonstrated by the topical application to the test insect of a solution of the compound under test in cellosolve (+1% piperonyl butoxide). Mortality was assessed at 48 hours. Compound 1 was active at <0.25 µg/insect.

*Spodoptera littoralis*

The activity of compounds of the invention against 3rd instar larvae was demonstrated by the topical application to the test insect of 0.5 µl of a solution of the compound under test in acetone (with or without 50 µg piperonyl butoxide). Mortality was assessed up to 48 hours. Compound 1 was active at <5 µg/insect. The following compounds were active at up to 10 µg per larva (+50 µg piperonyl butoxide): 33,40,41,47,38

*Plutella xylostella*

7 Plutella larvae were sprayed with the solution containing the compound and added to a chinese cabbage leaf which has been similarly sprayed and left to dry. Alternatively 8-10 Plutella larvae were put onto leaf discs and sprayed with the solution containing the compound. Mortality was assessed after 2 days at 25°.

The following compounds were active at 8 ppm:
1,2,3,5,10,11,12,14,22,23,C4,C5

SCHEME 1 - Preparation of amides of formula (1)

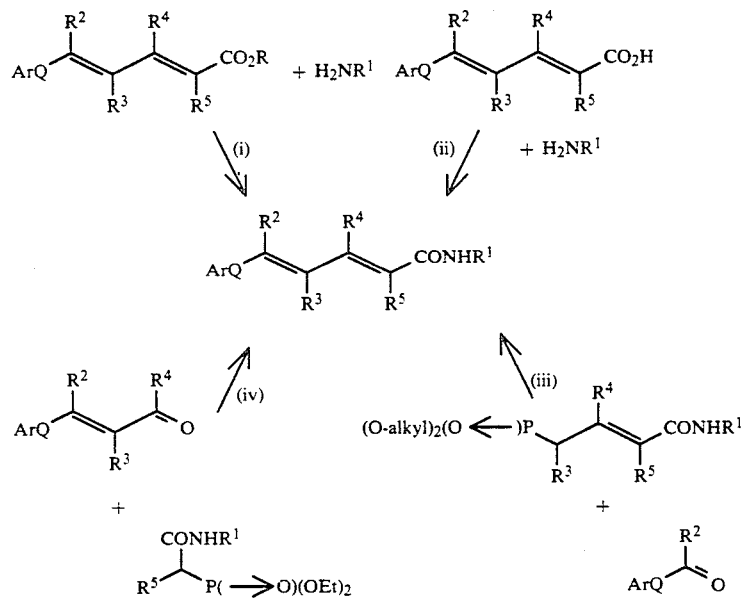

(i) Process (a), $Z^1$ = OR
(ii) Process (a), $Z^1$ = OH
(iii) Process (b), a = 1
(iv) Process (b), a = 1

SCHEME 2 - Preparation of ester intermediate $ArQQ^1COR$

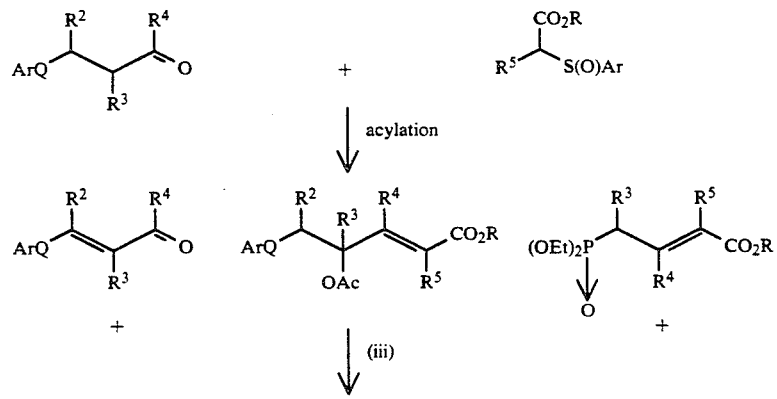

-continued
SCHEME 2 - Preparation of ester intermediate ArQQ¹COR
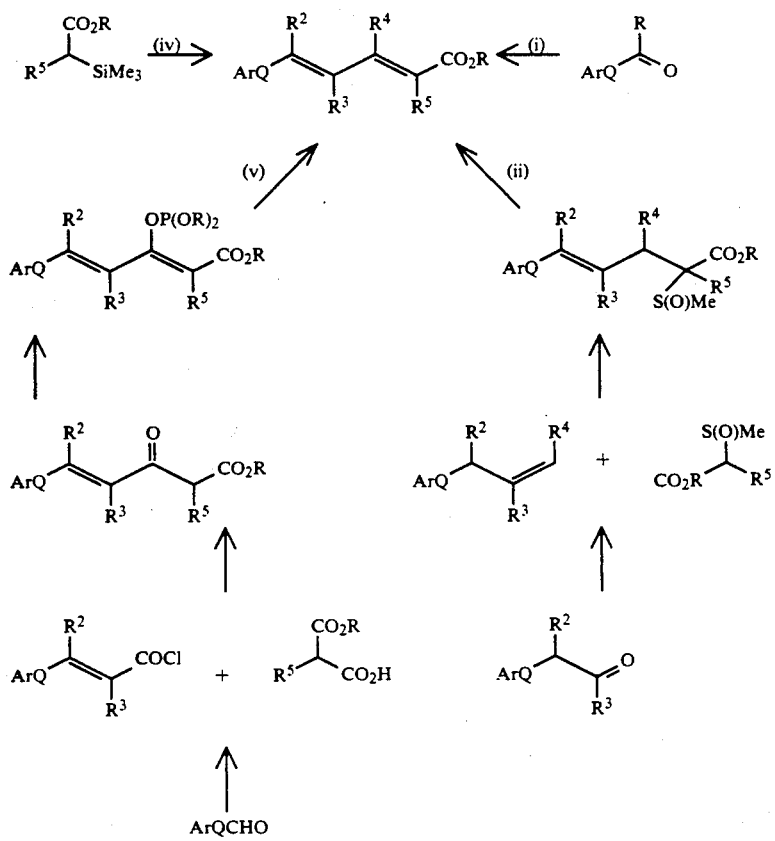
(i)–(v) denote processes (i) to (v) described hereinbefore for preparation of ester intermediates L = leaving group as defined in process description above.
SCHEME 3 - Preparation of alcohol and aldeyde intermediates
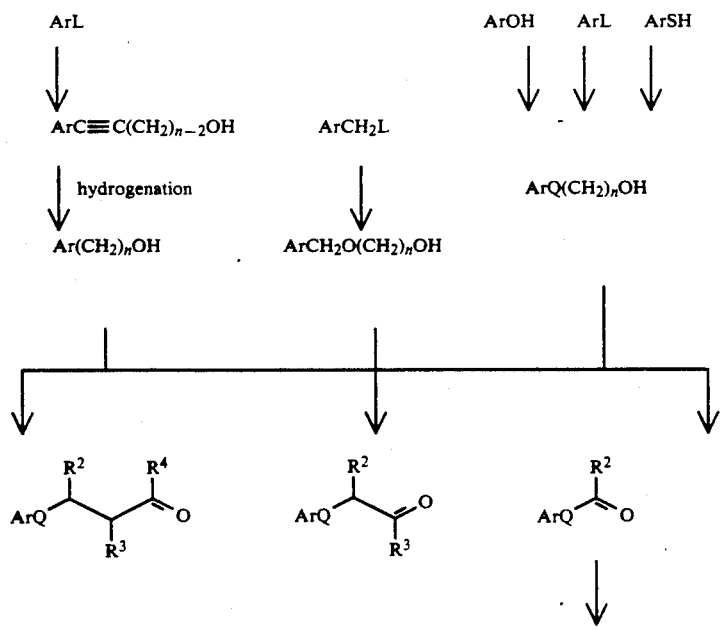

-continued
SCHEME 3 - Preparation of alcohol and aldehyde intermediates

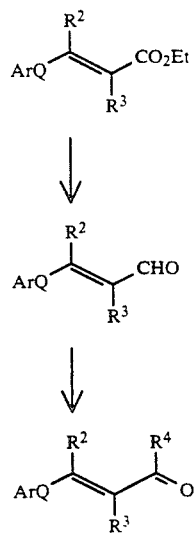

L = leaving group as defined in process description above.

SCHEME 4 - Preparation of thioamides of formula (1)

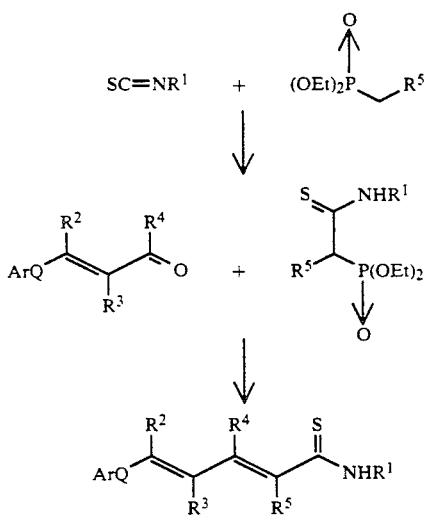

(i) Process (b). a = 1

What we claim is:
1. A compound of the formula (I):

ArQQ$^1$C(=X)NHR$^1$ or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; Q$^1$ is a group (C(R$^2$)=C(R$^3$))$_a$—(C(R$^4$)=C(R$^5$)) wherein a is 0 or 1, R$^2$, R$^3$, R$^4$ and R$^5$ are the same or different, at least two being hydrogen and the other two being independently selected from hydrogen, halo, C$_{1-4}$ alkyl or C$_{1-4}$ haloalkyl; X is oxygen or sulphur; and R$^1$ is selected from hydrogen and C$_{1-8}$ hydrocarbon optionally substituted by dioxalanyl, halo, cyano, trifluoromethyl, trifluoromethylthio or C$_{1-6}$ alkoxy.

2. A compound of the formula (1) according to claim 1 wherein Ar is unsubstituted or substituted by up to three substituents selected from halo, cyano and C$_{1-6}$ alkyl and C$_{1-6}$ alkoxy each optionally substituted by one to five halos or from a group S(O)$_m$R$^6$ wherein m is 0, 1 or 2 and R$^6$ is C$_{1-6}$ alkyl optionally substituted by halo.

3. A compound of the formula (1) according to claim 1 wherein Ar is unsubstituted or substituted by one or two of alkyl, halo or CF$_3$.

4. A compound of the formula (1) according to claim 1 wherein an additional ring heteroatom is sulphur.

5. A compound of the formula (1) according to claims 1 wherein R$^2$, R$^3$ and R$^5$ are all hydrogen and R$^4$ is hydrogen or methyl.

6. A compound of the formula (1) according claim 1 wherein R$^1$ selected from isobutyl, 1,2-dimethylpropyl, 1,1,2-trimethylpropyl, 2,2-dimethylpropyl, or R$^1$ is 2-methyl-prop-2-enyl or 2-methyl-1,3-dioxalan-2-yl.

7. A compound of the formula (II) according to claim 1:

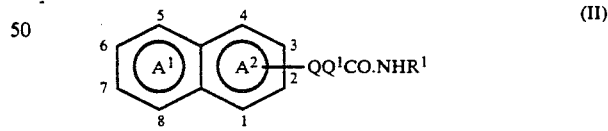

wherein one of the rings A$^1$ and A$^2$ is an aromatic ring containing a nitrogen atom and the other is a C$_6$-carbocylic aromatic ring, the side chain is attached at position 1 or 2, and Q, Q$^1$ and R$^1$ are as defined in claim 1.

8. A compound of the formula (III):

or a salt thereof wherein Q, Q$^1$, and R$^1$ are as defined in claim 1.

9. A compound selected from:
(2E,4E,/2Z,4E)N-Isobutyl 3-methyl-12-(2-quinolinyloxy)-dodeca -2-4-dienamide
(2E,4E) N-Isobutyl 12-(2-quinolinoxy)-dodeca-2,4-dienamide
(2E,4E) N-Isobutyl 3-methyl-12-(2-quinolinoxy)-dodeca-2, 4-dienamide
(2E,4E) N-1,1,2,-Trimethylpropyl 12-(2-quinolinyloxy)-dodeca-2, 4-dienamide
(2E,4E) N-2,2-Dimethylpropyl 12-(2-quinolinyloxy)-dodeca-2, 4-dienamide
(2E,4E) N-(2-Methyl-1,3-dioxolan-2-yl)methyl 12-(2-quinolinyloxy) -dodeca-2,4-dienamide
(2E,4E) N-1,2-dimethylpropyl 12-(2-quinolinyloxy)-dodeca-2, 4-dienamide
(2E/Z,4E) N-2-Methyl-prop-2-enyl 3-methyl-12-(2-quinolinyloxy)-dodeca-2,4-dienamide
(2E/Z,4E) N-1-Methylpropyl 3-methyl-12-(2-quinolinyloxy)-dodeca-2,4- dienamide
(2E,4E) N-Isobutyl 12-(4-methyl-2-quinolinyloxy)-dodeca-2, 4-dienamide
(2E/Z,4E) N-Isobutyl 3-methyl-12-(4-methyl-2-quinolinyloxy) -dodeca-2,4-dienamide
(2E/Z,4E) N-2-Methylprop-2-enyl 3-methyl-12-(4-methyl-2-quinolinyloxy) -dodeca-2,4-dienamide
(2E,4E) N-1,2-dimethylpropyl 12-(4-methyl-2-quinolinyloxy)-dodeca-2,4-dienamide
(2E,Z,4E) N-Isobutyl 3-methyl-12-(4-chloro-2-quinolinyloxy)-dodeca-2,4-dienamide
(2E,4E) N-Isobutyl 12-(4-chloro-2-quinolinyloxy)-dodeca-2,4-dienamide
(2Z,4E) N-Isobutyl-2-fluoro-3-methyl-12-(2-quinolinyloxy)dodeca-2,4-dienamide
(2E,4Z) N-Isobutyl-4-fluoro-12-(2-quinolinyloxy)-dodeca-2,4-dienamide
(2E,4Z) N-Isobutyl-4-fluoro-3-methyl12-(2-quinolinyloxy)dodeca-2,4-dienamide
(2E,4E) N-Isobutyl 3-methyl-12-(4-trifluoromethyl-2-quinolinyloxy)-dodeca-2,4-dienamide
(2E/Z,4E) N-Isobutyl 3-methyl-12-(6-bromo-2-quinolinyloxy)-dodeca-2,4-dienamide
(2E,4E) N-Isobutyl 12-(6-bromo-2-quinolinyloxy)-dodeca-2,4-dienamide
(2E/Z,4E) N-Isobutyl 3-methyl-12-(6-iodo-2-quinolinyloxy)-dodeca-2,4-dienamide
(2E/Z,4E) N-Isobutyl 3-methyl-12-(6-fluoro-2-quinolinyloxy)-dodeca-2,4-dienamide
(2E/Z,4E) N-Isobutyl 3-methyl-12-(3-bromo-2-quinolinyloxy)dodeca-2,4-dienamide
(2E/Z,4E) N-Isobutyl 3-methyl-12-(3-fluoro-2-quinolinyloxy)-dodeca-2,4-dienamide
(2E/Z,4E) N-Isobutyl 3-methyl-12-(8-fluoro-2-quinolinyloxy)-dodeca-2,4-dienamide
(2E,4E) N-Isobutyl 12-(6-chloro-2-quinolinyloxy)-dodeca-2,4-dienamide
(2E/Z,4E) N-Isobutyl 3-methyl-12-(6-chloro-2-quinolinyloxy) dodeca-2,4-dienamide
(2E,4E) N-Isobutyl 12- (6-trifluoromethyl-2-quinolinyloxy) dodeca-2,4-dienamide
(2E/Z,4E) N-Isobutyl 3-methyl-12-(6-trifluoromethyl-2-quinolinyloxy)dodeca-2,4-dienamide
(2E/Z,4E) N-Isbutyl 3-methyl-12-(3-chloro-2-quinolinyloxy)dodeca-2,4-dienamide
(2E/Z,4E) N-Isobutyl 3-methyl-12-(4-methoxy-2-quinolinyloxy) dodeca-2,4-dienamide
(2E/Z,4E) N-Isobutyl 3-methyl-12-(3-cyano-2-quinolinyloxy) dodeca-2,4-dienamide
(2E/Z,4E) N-Isobutyl 3-methyl-12-(3-nitro-2-quinolinyloxy) dodeca-2,4-dienamide
(2E/Z,4E) N-Isobutyl 3-methyl-12-(8-chloro-2-quinolinyloxy) dodeca-2,4-dienamide.

10. A compound of the formula (III):

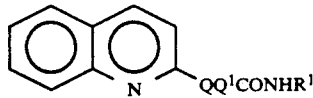

or a salt thereof wherein Q and $Q^1$ form a group $OQ^3CH=CR^3-CR^4=CR^5$ wherein $Q^3$ is $(CH_2)_7$, $R^4$ is hydrogen or methyl and $R^3$ and $R^5$ are hydrogen or fluoro.

11. A pesticidal formulation comprising a compound of formula (I)

$$ArQQ^1C(=X)NHR^1 \qquad (I)$$

or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; $Q^1$ is a group $(C(R^2)=C(R^3))_a-(C(R^4)=C(R^5))$ wherein a is 0 or 1, $R^2$, $R^3$, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoromethyl, trifluoromethylthio or $C_{1-6}$ alkoxy in admixture with one or more carriers or diluents.

12. A method for the control of arthropod or helminth pests which comprises administering to the arthropod or helminth or their environment and effective amount of the compound of formula (I)

$$ArQQ^1C(=X)NHR^1 \qquad (I)$$

or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; $Q^1$ is a group $(C(R^2)=C(R^3))_a-(C(R^4)=C(R^5))$ wherein a is 0 or 1, $R^2$, $R^3$, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoromethyl, trifluoromethylthio or $C_{1-6}$ alkoxy to the plane susceptible to pest infestation.

13. A method for the control of pesticidal infestation on plants which comprises administering an effective amount of the compound of formula (I)

$$ArQQ^1C(=X)NHR^1 \qquad (I)$$

or a salt thereof, wherein Ar is selected from quinoline, isoquinoline, quinoxaline, cinnoline, quinazline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; $Q^1$ is a group $(C(R^2)=C(R^3))_a-(C(R^4)=C(R^5))$ wherein a is 0 or 1, $R^2$, $R^3$, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoromethyl, trifluoromethylthio or $C_{1-6}$ alkoxy to the plant susceptible to pest infestation.

14. A method for the control of pesticidal infestation on stored products which comprises administering an effective amount of the compound of formula (I)

$$ArQQ^1C(=X)NHR^1 \quad (I)$$

or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; $Q^1$ is a group $(C(R^2)=C(R^3))_a-(C(R^4)=C(R^5))$ wherein a is 0 or 1, $R^2$, $R^3$, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoromethyl, trifluoromethylthio or $C_{1-6}$ alkoxy to the stored product susceptible to pest infestation.

15. A method for the control of pesticidal infestation on an environment which comprises administering an effective amount of the compound of formula (I)

$$ArQQ^1C(=X)NHR^1 \quad (I)$$

or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur of one oxygen atom adjacent to the Ar ring system; $Q^1$ is a group $(C(R^2)=C(R^3))_a-(C(R^4)=C(R^5))$ wherein a is 0 or 1, $R^2$, R, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoromethyl, trifluoromethylthio or $C_{1-6}$ alkoxy to the environment susceptible to pest infestation.

16. A method for the control of pesticidal infestations on animals which comprises administering to the animal an effective amount of the compound of formula (I)

$$ArQQ^1C(=x)NHR^1 \quad (I)$$

or a salt thereof, wherein Ar is selected from quinoline, isoquinoline, quinoxaline, cinnoline, quinazoline, phthalazine, benzothiazole, naphthyridine, tetrahydroquinoline and tetrahydroisoquinoline; Q is an alkyl chain containing 1 to 12 carbon atoms and optionally containing a sulphur or one oxygen atom adjacent to the Ar ring system; $Q^1$ is a group $(C(R^2)=C(R^3))_a-(C(R^4)=C(R^5))$ wherein a is 0 or 1, $R^2$, $R^3$, $R^4$, and $R^5$ are the same or different, at least two being hydrogen and the other two being independently selected from hydrogen, halo, $C_{1-4}$ alkyl or $C_{1-4}$ haloalkyl; X is oxygen or sulphur; and $R_1$ is selected from hydrogen and $C_1$-$C_8$ hydrocarbyl optionally substituted by dioxalanyl, halo, cyano, trifluoroemethyl, trifluoromethylthio or $C_{1-6}$ alkoxy.

* * * * *